US012611225B2

(12) United States Patent
Horie et al.

(10) Patent No.: US 12,611,225 B2
(45) Date of Patent: Apr. 28, 2026

(54) PUNCTURE NEEDLE AND NEEDLE ASSEMBLY

(71) Applicant: TERUMO KABUSHIKI KAISHA, Tokyo (JP)

(72) Inventors: Madoka Horie, Minami-Alps (JP); Takeshi Akiyama, Chuo (JP); Eiki Kimura, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 187 days.

(21) Appl. No.: 18/504,875

(22) Filed: Nov. 8, 2023

(65) Prior Publication Data

US 2024/0065727 A1     Feb. 29, 2024

Related U.S. Application Data

(63) Continuation of application No. PCT/JP2021/032003, filed on Aug. 31, 2021.

(51) Int. Cl.
A61B 17/34 (2006.01)

(52) U.S. Cl.
CPC ................................ A61B 17/3417 (2013.01)

(58) Field of Classification Search
CPC ............ A61B 17/3417; A61B 17/3468; A61B 17/3474; A61B 17/3478; A61B 5/150282;
(Continued)

(56) References Cited

U.S. PATENT DOCUMENTS 2,560,162 A * 7/1951 Ferguson ............ A61M 5/3286
D24/112
2010/0036281 A1 * 2/2010 Doi .................. A61B 5/150358
600/583
(Continued)

FOREIGN PATENT DOCUMENTS

JP        H08-187237 A        7/1996
WO     WO-2013/035455 A1     3/2013
WO     WO-2021/039334 A1     3/2021

OTHER PUBLICATIONS

Written Opinion of the International Searching Authority issued in the corresponding International Patent Application No. PCT/JP2021/032003, dated Oct. 26, 2021 with English translation.
(Continued)

*Primary Examiner* — Kathleen S Holwerda
(74) *Attorney, Agent, or Firm* — Foley & Lardner LLP

(57) ABSTRACT

A puncture needle according to the present disclosure includes a puncture portion having a blade surface at a distal-end surface; and a retained portion connected to a proximal-end puncture-portion side and configured to be retained by a hub. The puncture portion includes a slit extending to the distal-end surface. The retained portion includes: a tubular portion having a substantially constant outer diameter larger than a maximum outer diameter of the puncture portion, and a tapered portion located between the puncture portion and the tubular portion, an outer diameter of the tapered portion gradually decreasing from a tubular-portion side to a puncture-portion side, wherein in a lateral view with the slit facing upward, lower contour lines of the puncture portion, the tubular portion, and the tapered portion are collinear.

5 Claims, 20 Drawing Sheets

(58) Field of Classification Search
    CPC ........ A61B 5/150396; A61B 5/150404; A61B
                        5/150503; A61B 5/150511; A61B
                    5/150519; A61M 5/3286; A61M 25/06
    See application file for complete search history.

(56)                     References Cited

U.S. PATENT DOCUMENTS

| | | |
|---|---|---|
| 2016/0243305 A1 | 8/2016 | Nakamura et al. |
| 2017/0265791 A1 | 9/2017 | Pace et al. |

OTHER PUBLICATIONS

International Search Report and Written Opinion of the International Searching Authority issued in the corresponding International Patent Application No. PCT/JP2021/032003, dated Oct. 26, 2021.
Office Action issued in Japanese Appl. No. 2023-544845 dated Mar. 18, 2025.

* cited by examiner

PUNCTURE NEEDLE AND NEEDLE ASSEMBLY

CROSS-REFERENCE TO RELATED APPLICATIONS

This is a bypass continuation of PCT Application No. PCT/JP2021/032003, filed on Aug. 31, 2021, the entire contents of which are incorporated herein by reference.

BACKGROUND

The present disclosure relates to a puncture needle and a needle assembly.

There is a case in which a medical instrument such as a sensor is embedded in a living body of a subject such as a patient. For example, a sensor is embedded in the living body of the subject, and an analyte (for example, glucose, pH, cholesterol, protein, and the like) in the blood or body fluid of the subject is monitored. In this case, a puncture tool is used to penetrate the skin of the subject and quickly and easily embed the sensor in the living body. U.S. Pat. Pub. No. 2017/265791 A ("Patent Literature 1") and PCT Pub. No. WO 2013/035455 A ("Patent Literature 2") disclose this type of puncture tool. In the puncture tool described in Patent Literature 1, a sensor is inserted into a living body together with a puncture needle, the sensor is indwelled under the skin, and only the puncture needle is removed from the living body.

In the puncture tools described in Patent Literature 1 and Patent Literature 2, the indwelling of the sensor in the living body and the indwelling of an electronic device such as a transmitter connected to the sensor on the living body surface are performed in conjunction with the insertion and removal operations of the puncture needle. In such a case, it is necessary to provide a puncture tool having a configuration for removing the puncture needle while avoiding a contact portion between the sensor and the electronic device. Therefore, in the puncture tools described in Patent Literature 1 and Patent Literature 2, a U-shaped or V-shaped puncture needle in which a slit is formed is used. In addition, Patent Literature 1 discloses an example in which the proximal-end side of such a puncture needle has a length passing through a hub that holds the puncture needle. Furthermore, Patent Literature 2 discloses a configuration in which a pair of winged portions is provided on the puncture needle.

SUMMARY

The puncture needles described in Patent Literature 1 and Patent Literature 2 preferably have a small diameter in order to reduce the pain of the subject. In addition, in the puncture needle described in Patent Literature 1 and Patent Literature 2 in which the slit is formed, the attachment area to the hub and the application amount of the adhesive for adhering to the hub may be smaller than those of the tubular needle. Therefore, the joint strength of the puncture needle to the hub may become a problem. In Patent Literature 1, a proximal-end side of a slit needle as the puncture needle is lengthened so as to pass through the hub, thereby increasing the attachment area of the puncture needle to the hub and securing joint strength to the hub. In addition, in Patent Literature 2, a pair of wing-shaped portions provided on a slit needle as a puncture needle is attached to a head as the hub, thereby securing joint strength to the head.

However, in the puncture needles described in Patent Literature 1 and Patent Literature 2, there is still room for improvement from the viewpoint of simplifying the configuration for securing the connection strength to the hub.

An object of the present disclosure is to provide a puncture needle and a needle assembly that achieve reduction in pain of a subject and improvement in joint strength to a hub with a simple configuration.

According to a first aspect of the present disclosure, a puncture needle includes a puncture portion having a blade surface at a distal-end surface; and a retained portion connected to a proximal-end puncture-portion side and configured to be retained by a hub, the puncture portion including a slit extending to the distal-end surface, and the retained portion including: a tubular portion having a substantially constant outer diameter larger than a maximum outer diameter of the puncture portion, and a tapered portion located between the puncture portion and the tubular portion, an outer diameter of the tapered portion gradually decreasing from a tubular-portion side to a puncture-portion side, wherein in a lateral view with the slit facing upward, lower contour lines of the puncture portion, the tubular portion, and the tapered portion are collinear.

According to one embodiment of the present disclosure, the slit extends from the distal-end surface of the puncture portion to the tapered portion of the retained portion.

According to one embodiment of the present disclosure, the slit is terminated at the tapered portion.

According to one embodiment of the present disclosure, the width of the slit gradually decreases toward a proximal end in the tapered portion.

According to one embodiment of the present disclosure, an outer diameter of the puncture portion is substantially constant on a proximal-end side relative to the distal-end surface.

According to another aspect of the present disclosure, a needle assembly includes the puncture needle and a hub that holds the retained portion of the puncture needle.

According to the present disclosure, it is possible to provide a puncture needle and a needle assembly that achieve reduction in pain of a subject and improvement in joint strength to a hub with a simple configuration.

DETAILED DESCRIPTION

Figure 1:
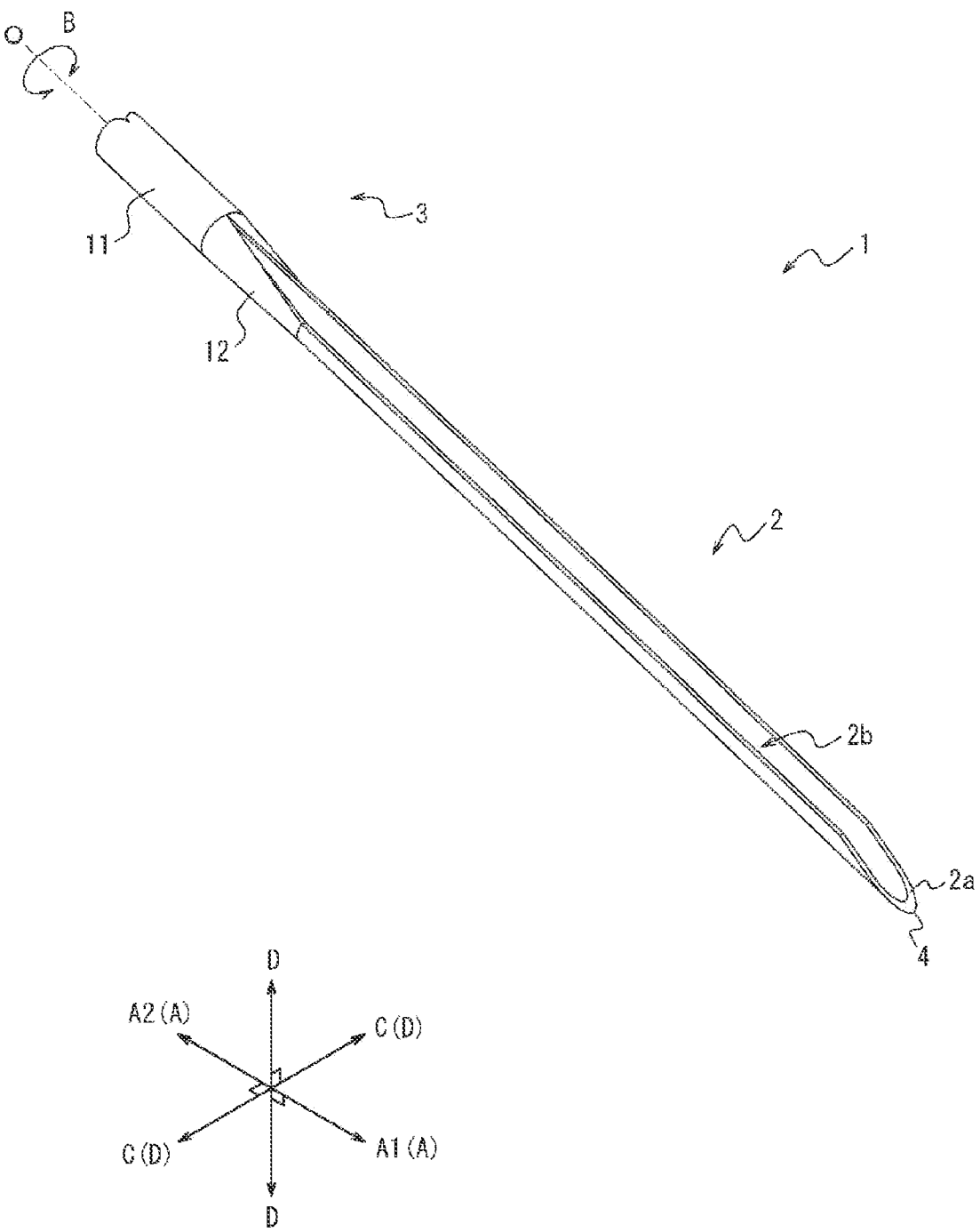
FIG. 1 is a perspective view of a puncture needle as one embodiment of the present disclosure.

Hereinafter, embodiments of a puncture needle and a needle assembly according to the present disclosure will be described by way of example with reference to the drawings. In the drawings, the same components are denoted by the same reference numerals.

[Puncture Needle]

Figure 2:
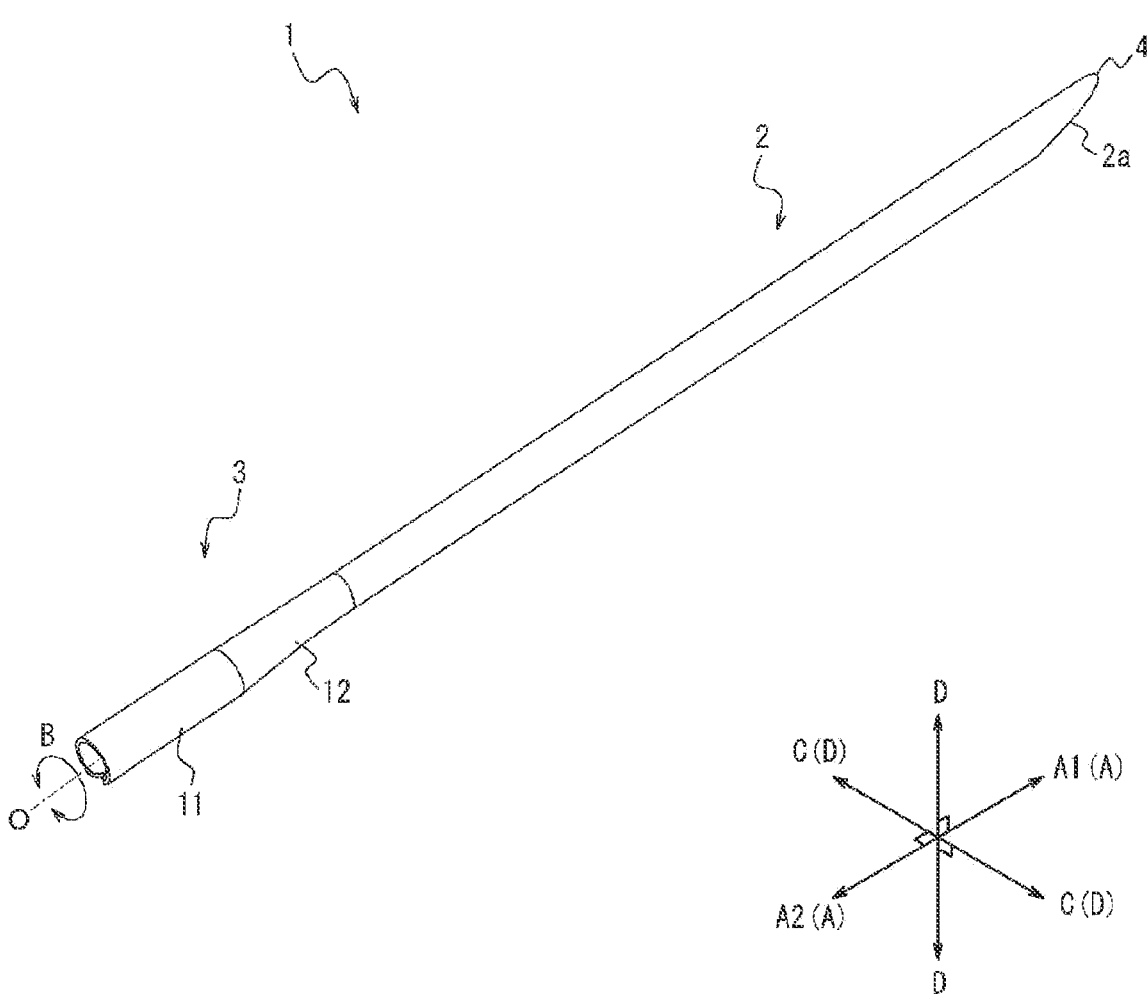
FIG. 2 is a perspective view of the puncture needle shown in FIG. 1 as viewed from a viewpoint different from that in FIG. 1.

FIG. 1 is a perspective view of a puncture needle 1 as one embodiment of a puncture needle according to the present disclosure. FIG. 2 is a perspective view of the puncture needle 1 as viewed from a viewpoint different from that in FIG. 1. Hereinafter, in the present description, a distal end of the puncture needle 1 in the longitudinal direction A in which a living body is punctured will be referred to as a "distal end." In the puncture needle 1, a proximal end opposite to the distal end in the longitudinal direction A will be referred to as a "proximal end." In the longitudinal direction A, a direction from the proximal end to the distal end of the puncture needle 1 may be referred to as an "insertion direction A1." Furthermore, in the longitudinal direction A, a direction from the distal end to the proximal end of the puncture needle 1 may be referred to as a "removal direction A2."

As shown in FIGS. 1 and 2, the puncture needle 1 includes a puncture portion 2 and a retained portion 3. As shown in FIG. 1, the puncture portion 2 includes a blade surface 2*a* on the distal-end surface. As shown in FIG. 1, the puncture portion 2 includes a slit 2*b* extending in the longitudinal direction A. The slit 2*b* extends to the distal-end surface. The retained portion 3 is connected to the proximal-end puncture-portion side 2. The retained portion 3 is configured so that the retained portion can be retained by a hub (for example, see "hub 50" shown in FIGS. 14 to 19).

Hereinafter, for convenience of description, a side surface of the puncture needle 1 on which the slit 2*b* is formed will be referred to as an "upper surface of the puncture needle 1." In addition, a side surface of the puncture needle 1 opposite to the side surface where the slit 2*b* is formed will be referred to as a "lower surface of the puncture needle 1." Further, when the puncture needle 1 is viewed from the proximal-end side toward the distal end in the longitudinal direction A, a side surface located on the right side of the slit 2*b* will be referred to as a "right side surface of the puncture needle 1," and a side surface located on the left side of the slit 2*b* will be referred to as a "left side surface of the puncture needle 1." Therefore, the perspective view of the puncture needle 1 shown in FIG. 1 is a perspective view showing the upper surface, the distal-end surface, and the right side surface of the puncture needle 1. The perspective view of the puncture needle 1 shown in FIG. 2 is a perspective view showing the lower surface, the proximal-end surface, and the left side surface of the puncture needle 1.

Figure 3:
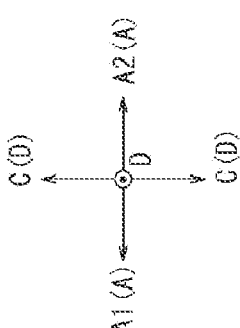
FIG. 3 is a top view of the puncture needle shown in FIG. 1.
Figure 4:
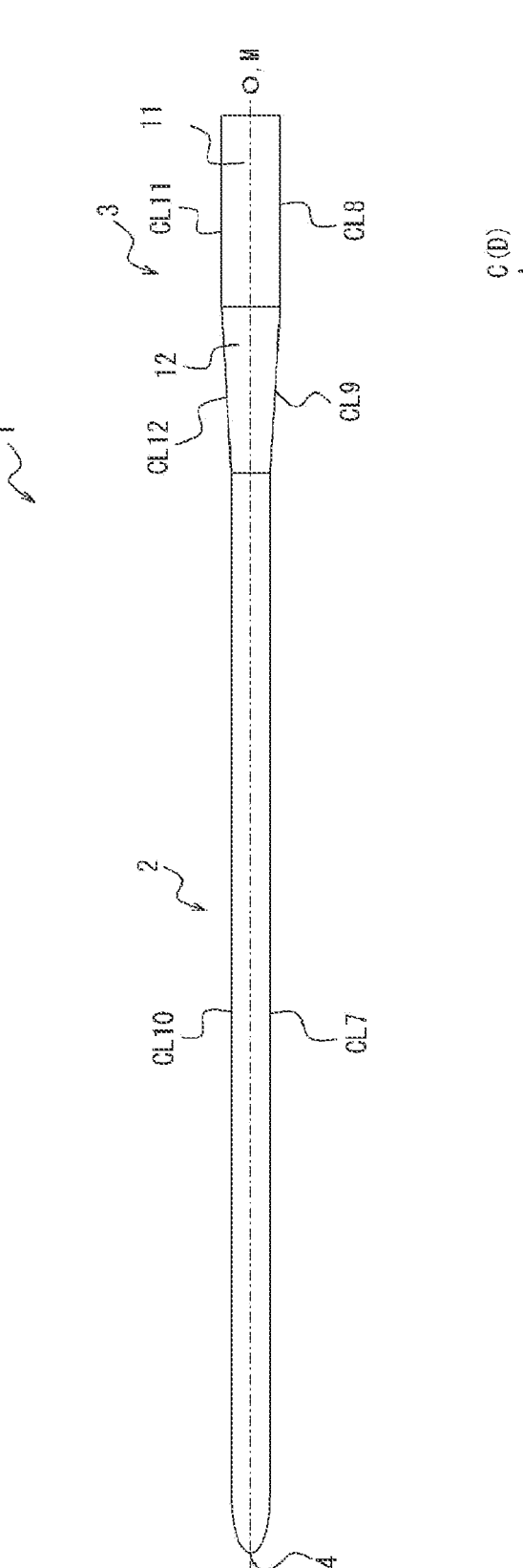
FIG. 4 is a bottom view of the puncture needle shown in FIG. 1.
Figure 5:
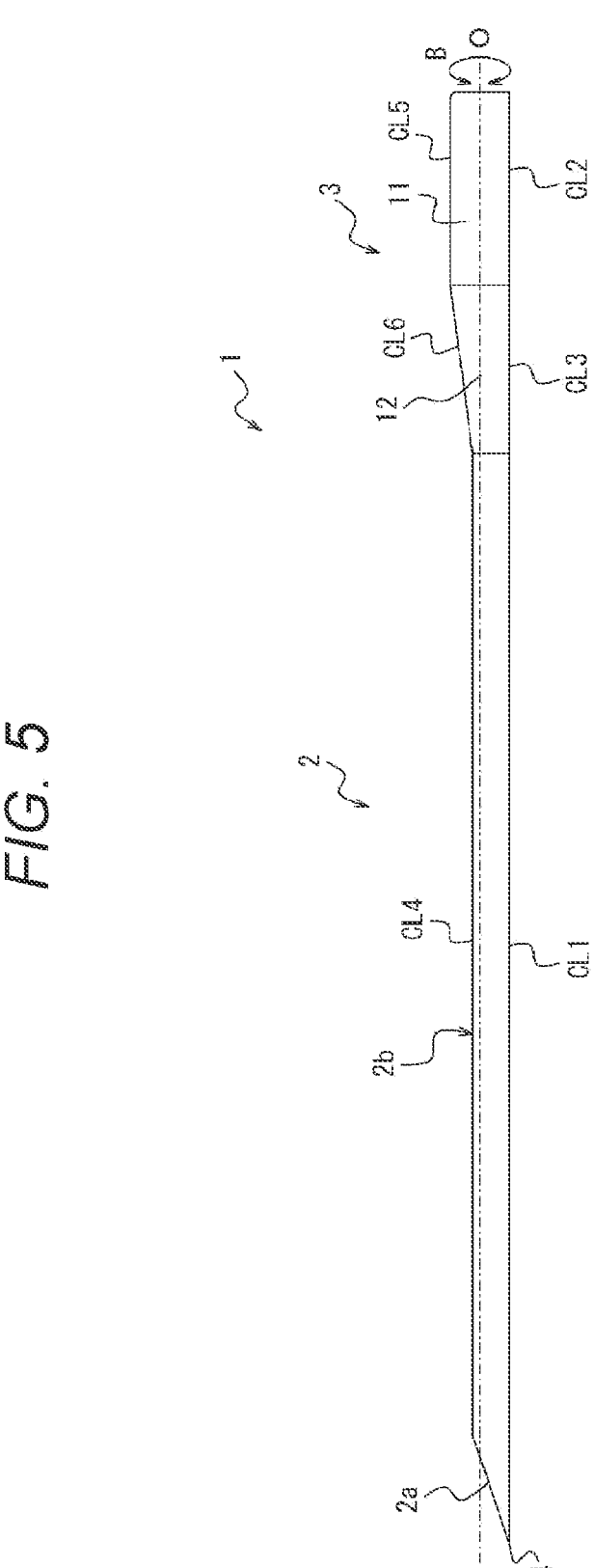
FIG. 5 is a left side view of the puncture needle shown in FIG. 1.
Figure 5:
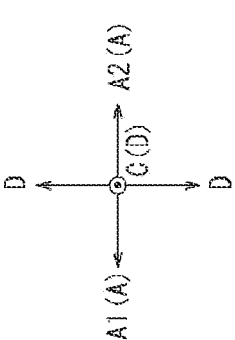
Figure 6:
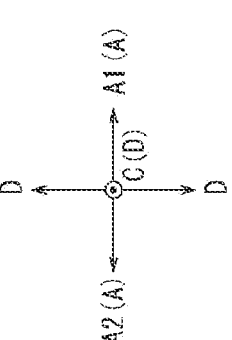
FIG. 6 is a right side view of the puncture needle shown in FIG. 1.
Figure 7:
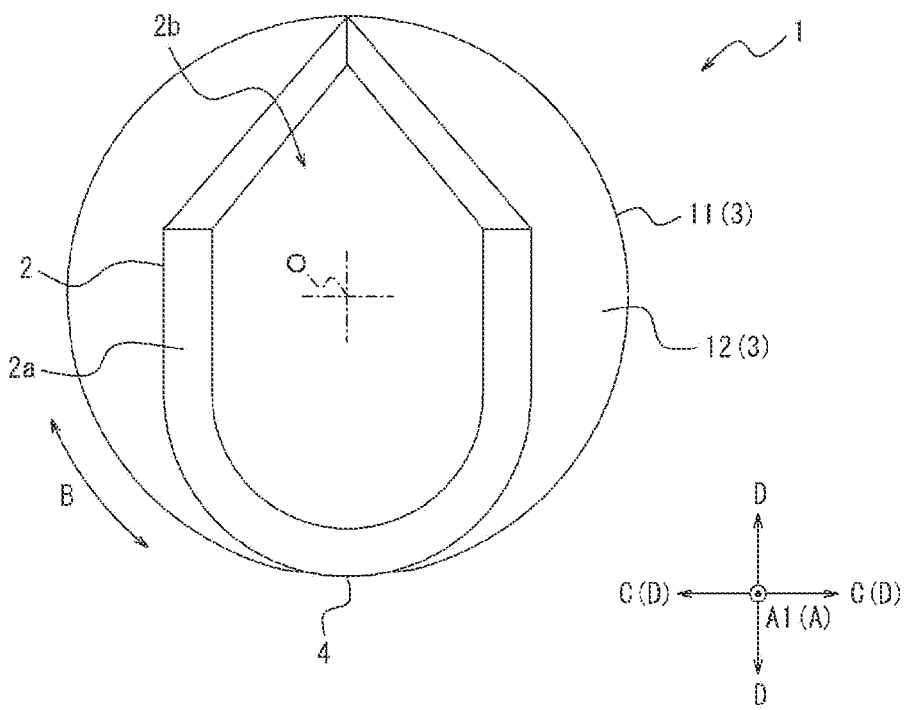
FIG. 7 is a distal-end view of the puncture needle shown in FIG. 1 as viewed from a distal-end surface side.
Figure 8:
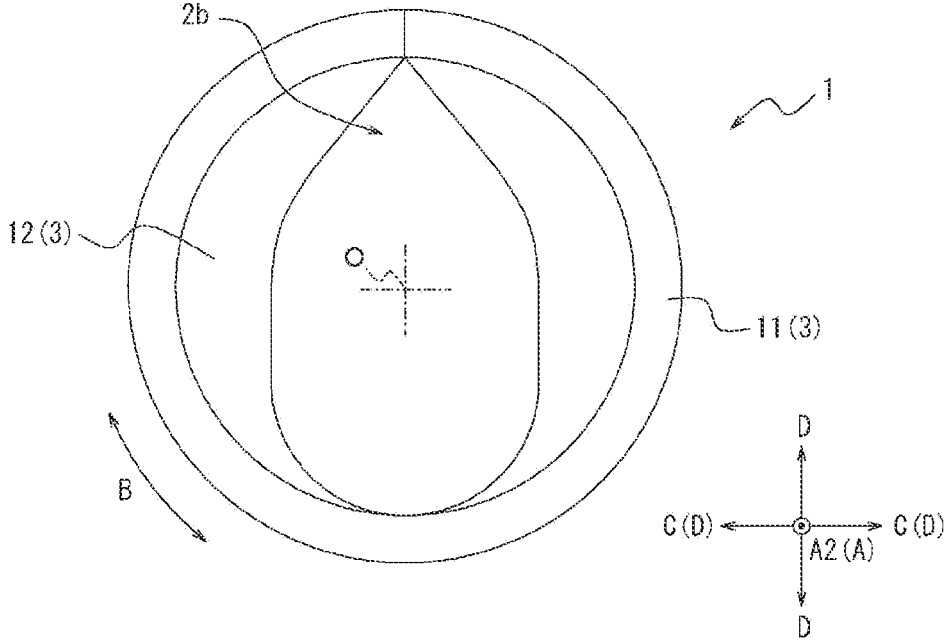
FIG. 8 is a proximal end view of the puncture needle shown in FIG. 1 as viewed from a proximal-end surface side.
Figure 9:
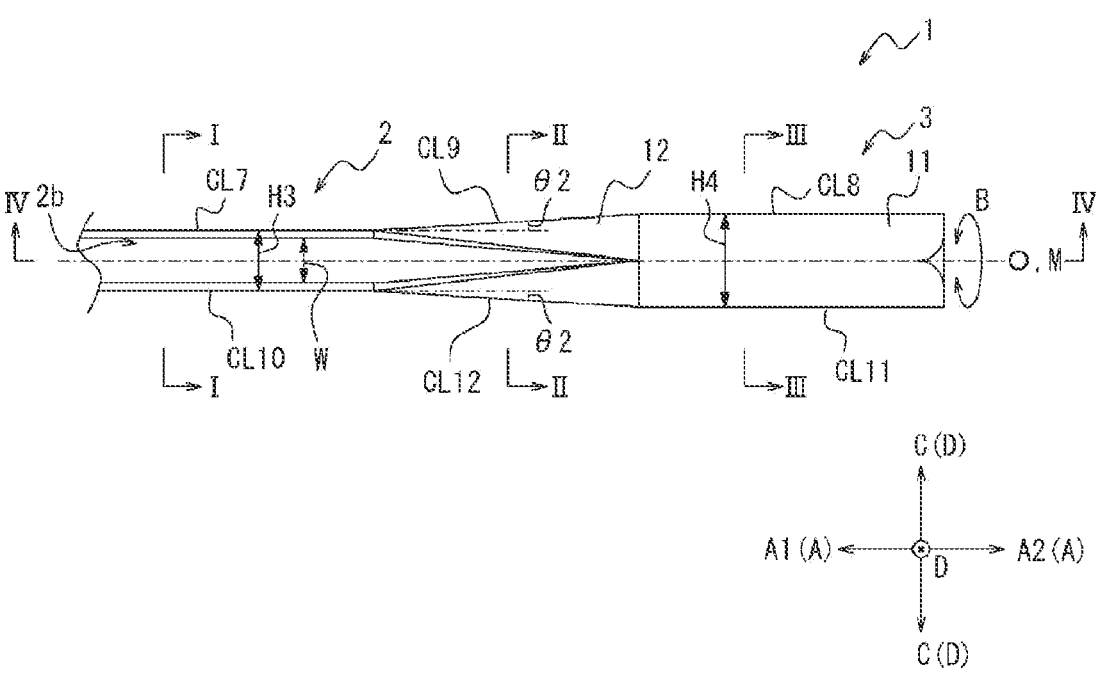
FIG. 9 is an enlarged top view in which a part of FIG. 3 is enlarged.
Figure 10:
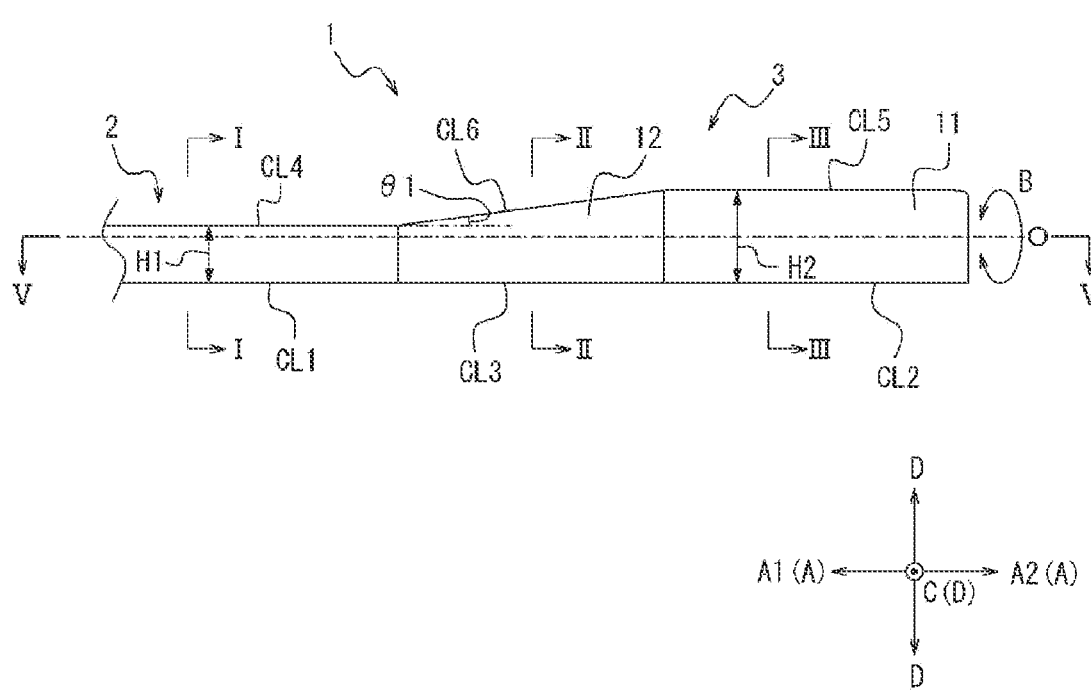
FIG. 10 is an enlarged left side view in which a part of FIG. 5 is enlarged.
Figure 11:
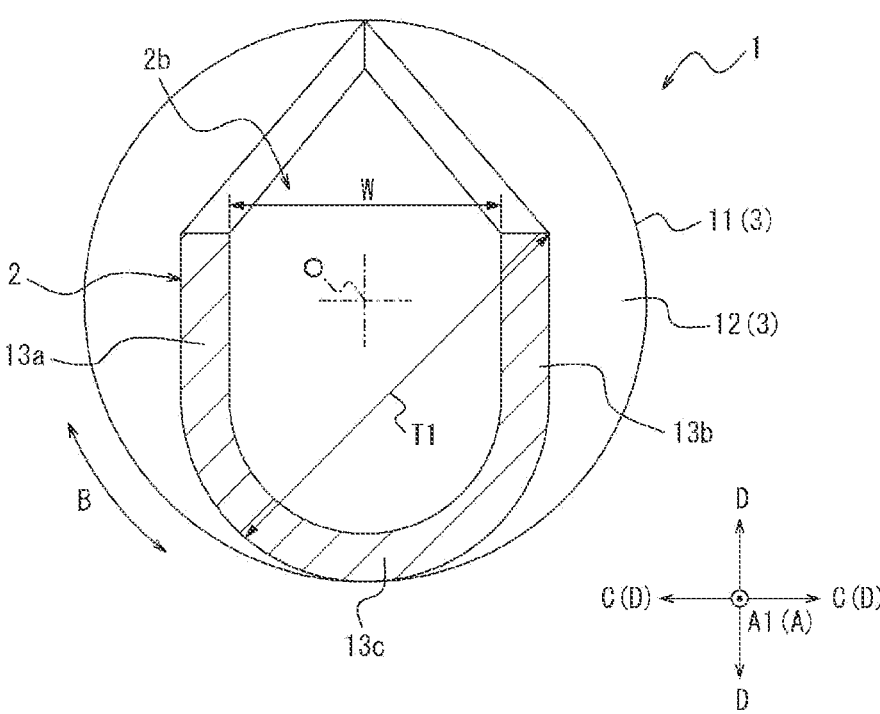
FIG. 11 is a cross-sectional view taken along line I-I in FIGS. 9 and 10.
Figure 12:
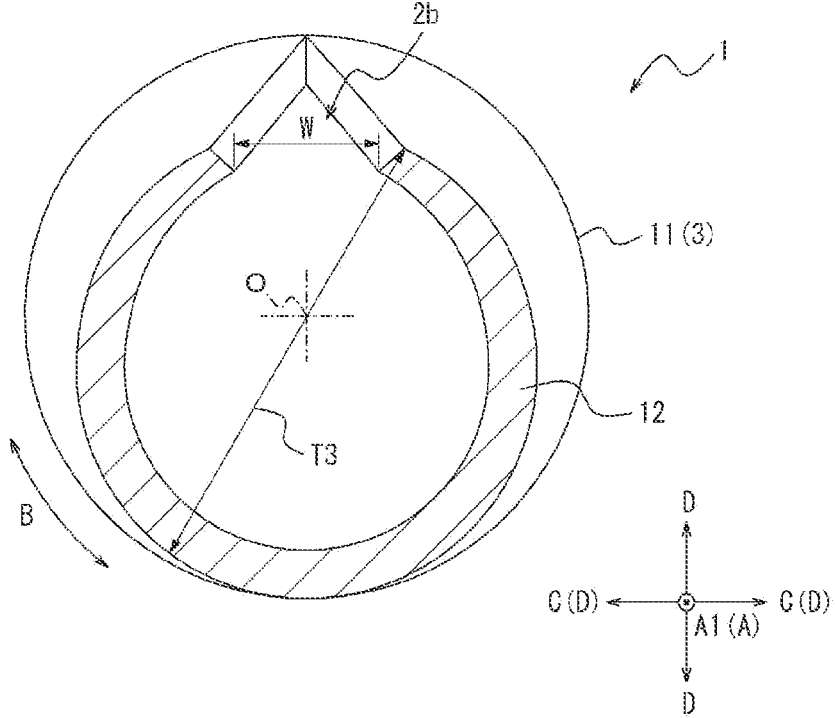
FIG. 12 is a cross-sectional view taken along line II-II in FIGS. 9 and 10.
Figure 13:
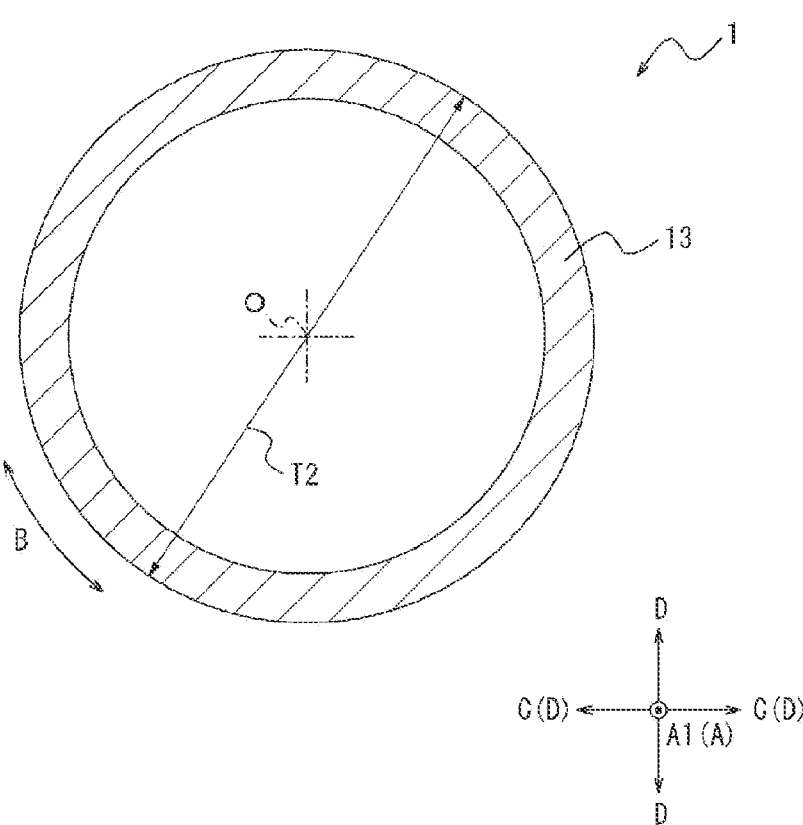
FIG. 13 is a cross-sectional view taken along line III-III in FIGS. 9 and 10.

FIG. 3 is a top view of the puncture needle 1. FIG. 4 is a bottom view of the puncture needle 1. FIG. 5 is a left side view of the puncture needle 1. FIG. 6 is a right side view of the puncture needle 1. FIG. 7 is a distal-end view of the puncture needle 1 as viewed from the distal-end surface side. FIG. 8 is a proximal-end view of the puncture needle 1 as viewed from the proximal-end surface side. FIG. 9 is an enlarged top view in which a part of the top view of the puncture needle 1 shown in FIG. 3 is enlarged. FIG. 10 is an enlarged left side view in which a part of the left side view of the puncture needle 1 shown in FIG. 5 is enlarged. FIG. 11 is a cross-sectional view of the puncture needle 1 taken along line I-I in FIGS. 9 and 10. FIG. 12 is a cross-sectional view of the puncture needle 1 taken along line II-II in FIGS. 9 and 10. FIG. 13 is a cross-sectional view of the puncture needle 1 taken along line III-III in FIGS. 9 and 10.

As shown in FIGS. 1 to 10, the retained portion 3 includes a tubular portion 11 and a tapered portion 12. The tubular portion 11 has a substantially constant outer diameter T2 (see FIG. 13). The outer diameter T2 of the tubular portion 11 is larger than an outer diameter T1 (see FIG. 11) of the puncture portion 2. More specifically, the outer diameter T2 of the tubular portion 11 is larger than a maximum outer diameter T1max of the puncture portion 2. As shown in FIG. 11, the outer diameter T1 of the puncture portion 2 means a maximum cross-sectional length in the cross section of the puncture portion 2 orthogonal to the longitudinal direction A. The maximum outer diameter T1max of the puncture portion 2 means a maximum value when the outer diameter T1 is compared at the position in the longitudinal direction A. As shown in FIG. 13, the outer diameter T2 of the tubular portion 11 means a maximum cross-sectional length in the cross section of the tubular portion 11 orthogonal to the longitudinal direction A. As shown in FIG. 13, when the outer shape of the cross section of the tubular portion 11 orthogonal to the longitudinal direction A is circular, the outer diameter T2 of the tubular portion 11 described above is the diameter of the outer peripheral surface of the tubular portion 11.

The tapered portion 12 is located between the puncture portion 2 and the tubular portion 11. An outer diameter T3 of the tapered portion 12 gradually decreases from the tubular portion 11 side toward the puncture portion 2 side. As shown in FIG. 12, the outer diameter T3 of the tapered portion 12 means a maximum cross-sectional length in the cross section of the tapered portion 12 orthogonal to the longitudinal direction A.

In this manner, the retained portion 3 configured to be capable of being retained by the hub (for example, see "hub 50" shown in FIGS. 14 to 19) includes the above-described tapered portion 12. As a result, the outer surface of the tapered portion 12 inclined with respect to the longitudinal direction A is easily fixed to the hub directly or indirectly via an adhesive or the like. As a result, it is difficult for the puncture needle 1 to be detached from the hub in the insertion direction A1. In the puncture needle 1, the retained portion 3 includes the tubular portion 11. As a result, it is possible to improve the joint strength of the puncture needle 1 to the hub as compared with a puncture needle having a configuration that has a slit over the entire length and does not include a tubular retained portion. Because the puncture needle 1 includes the tapered portion 12, the joint strength to the hub can be improved by the outer surface shape of the tapered portion 12. The puncture needle 1 can achieve high joint strength to the hub as compared with a puncture needle in which the retained portion is only a tubular portion. As a result, the length of the puncture needle 1 can be shortened, so that the size of the puncture tool can be reduced.

In addition, when the tapered portion 12 is provided, it is not necessary to increase the diameter of the puncture portion 2 on the distal-end side of the retained portion 3 for increasing the joint strength of the puncture needle 1 to the hub. In addition, providing the tapered portion 12 makes it easy to fix to the hub as described above. Providing the tubular portion 11 adjacent to the tapered portion 12 allows the outer diameter T2 of the tubular portion 11 to be set to 110 to 210% of the outer diameter T1max of the puncture portion 2. That is, providing the tubular portion 11 and the tapered portion 12 makes it possible to further increase the joint strength of the puncture needle 1 to the hub while keeping the puncture portion 2 to have the minimum cross-sectional length necessary for insertion of the sensor. Therefore, puncture resistance of the puncture portion 2 at the time of puncturing the living body can be reduced. In addition, the pain of the subject can be reduced.

As described above, according to the puncture needle 1, with a simple configuration in which the tapered portion 12 is provided on the retained portion 3, it is possible to realize pain reduction for the subject and improvement of the joint strength to the hub.

In addition, because the retained portion 3 includes the tubular portion 11, the assembly work of the puncture needle 1 to the hub (for example, see "hub 50" shown in FIGS. 14 to 19) is facilitated. Specifically, for example, the position of a central axis O of the tubular portion 11 of the retained portion 3 can be used for relative positioning work of the puncture needle 1 and the hub in a plane orthogonal to the longitudinal direction A. In this manner, using the tubular portion 11 can facilitate the assembly work of the puncture needle 1 to the hub.

Furthermore, as shown in FIGS. 5, 6, and 10, the lower contour lines of the puncture portion 2, the tubular portion 11, and the tapered portion 12 are linearly connected in a lateral view in which the slit 2b of the puncture portion 2 faces upward. That is, in the lateral view of FIGS. 5, 6, and 10, the lower contour line CL1 of the puncture portion 2, the lower contour line CL2 of the tubular portion 11, and the lower contour line CL3 of the tapered portion 12 are linearly connected. With such a configuration, the puncture needle 1 having excellent mass productivity can be achieved. Specifically, with the puncture portion 2, the tubular portion 11, and the tapered portion 12 of the puncture needle 1 being integrally supported on the side of the contour lines CL1, CL2, and CL3 linearly connected, the blade surface forming step of forming the blade surface on the distal-end surface of the puncture portion 2 can be easily performed. More specifically, with the contour lines CL1, CL2, and CL3 linearly connected, the puncture needle 1 can be accurately supported by a jig or the like. This makes it possible to accurately cut out the center of the blade surface while maintaining mass productivity. In addition, it is easy to apply arbitrary processing to the blade surface. The puncture needle 1 having the blade surface formed with high accuracy can reduce the pain of the subject as well as reduce the puncture resistance.

As a material of the puncture needle 1, for example, a metal material such as stainless steel, aluminum, an aluminum alloy, titanium, a titanium alloy, or a magnesium alloy can be used. As a material of the puncture needle 1, a material that can be manufactured by plastic working is selected. Examples of plastic working include cutting of a drawn pipe having a predetermined inner diameter and press working of a metal flat plate. Preferably, a material to which press working can be applied is selected as the material of the puncture needle 1.

Hereinafter, further details of the puncture needle 1 of the present embodiment will be described with reference to FIGS. 1 to 13.

<Puncture Portion 2>

As shown in FIGS. 1 to 6, etc., the puncture portion 2 of the present embodiment extends linearly in the longitudinal direction A. As shown in FIG. 1, etc., a blade surface 2a constituted by an inclined surface inclined with respect to the longitudinal direction A is formed on a distal-end surface of the puncture portion 2. A needle tip 4 of the puncture needle 1 is formed of a distal end which is a distal end of the blade surface 2a of the puncture portion 2. That is, the distal-end surface of the puncture needle 1 is formed of the distal-end surface of the puncture portion 2 in which the blade surface 2a is formed.

The blade surface 2a of the present embodiment is formed of one plane inclined with respect to the longitudinal direction A, but the blade surface 2a is not limited to this configuration. The blade surface 2a may include, for example, a plurality of planes inclined at different angles with respect to the longitudinal direction A. The blade surface 2a may include a curved surface inclined with respect to the longitudinal direction A.

As shown in FIG. 1, etc., the puncture portion 2 includes a slit 2b extending in the longitudinal direction A. The slit 2b of the present embodiment extends from the tapered portion 12 of the retained portion 3 to the distal-end surface of the puncture portion 2. With such a slit 2b, the length of the slit 2b in the longitudinal direction A can be sufficiently secured. In the present embodiment, the slit 2b can be arranged in the entire region in the longitudinal direction A on the portion on the distal-end side of the puncture needle 1 protruding from the retained portion 3 retained by the hub (for example, see "hub 50" shown in FIGS. 14 to 19) and exposed to the outside of the hub. Therefore, it is possible to suppress a contact portion 90 of a sensor 300 (see FIGS. 16 to 19) and a detector 106 (see FIGS. 16 to 19) to be described later from being caught by the proximal end of the slit 2b, being damaged or broken.

Further, as shown in FIGS. 1, 3, 9, etc., the slit 2b of the present embodiment terminates at the tapered portion 12. That is, the proximal-end side of the slit 2b of the present embodiment terminates at the position of the tapered portion 12. In other words, the proximal-end side of the slit 2b of the present embodiment terminates on the distal-end side relative to the tubular portion 11. Therefore, it is possible to secure an unterminated tubular portion 11 having an approximate constant outer diameter T2 and maintain the ease of assembly work of the puncture needle 1 into the hub (see, for example, "hub 50" shown in FIGS. 14 to 19). In addition, because the retained portion 3 has the tubular portion 11, the tubular portion 11 can ensure the same degree of adhesive strength as a so-called tubular needle. In addition, processing conventionally used in the tubular needle can be performed.

Furthermore, as shown in FIGS. 3 and 9, a width W of the slit 2*b* of the present embodiment gradually decreases toward the proximal end in the tapered portion 12. The width W of the slit 2*b* means a length of the slit 2*b* in a direction orthogonal to the extending direction of the slit 2*b* (longitudinal direction A in the present embodiment) in a top view (see FIGS. 3 and 9) when the puncture needle 1 is viewed from the slit 2*b* side. As shown in FIG. 3, the width W of the slit 2*b* of the present embodiment is constant regardless of the position in the longitudinal direction A in the puncture portion 2. On the other hand, the width W of the slit 2*b* of the present embodiment gradually decreases toward the proximal end in the tapered portion 12. As described above, the slit 2*b* of the present embodiment terminates at the tapered portion 12. The width W of the slit 2*b* closes toward the proximal end at a pitch of 3% to 100% per 1 mm of the axial length of the puncture needle 1 when the maximum slit width of the puncture portion 2 is 100%.

As shown in FIG. 11, the puncture portion 2 of the present embodiment is a U-shaped needle portion having a substantially U-shaped outer shape in a cross-sectional view orthogonal to the longitudinal direction A. The puncture portion 2 of the present embodiment has a substantially U-shaped outer shape in a cross-sectional view orthogonal to the longitudinal direction A at an arbitrary position in the longitudinal direction A. In other words, as shown in FIG. 11, the puncture portion 2 of the present embodiment includes opposing side wall portions 13*a* and 13*b*, and a bottom portion 13*c* continuous with the side wall portions 13*a* and 13*b*. The bottom portion 13*c* is located on the lower surface side of the puncture needle 1.

As shown in FIG. 11, the side wall portions 13*a* and 13*b* of the present embodiment are formed of flat plate portions extending substantially linearly in a cross-sectional view orthogonal to the longitudinal direction A, but the present invention is not limited to this configuration. The side wall portions 13*a* and 13*b* may be formed of curved plate portions extending in an arc shape smoothly connected to the bottom portion 13*c* of the present embodiment in a cross-sectional view orthogonal to the longitudinal direction A. In other words, the puncture portion 2 of the present embodiment may be a C-shaped needle portion having a substantially C-shaped outer shape in a cross-sectional view orthogonal to the longitudinal direction A. In addition, the puncture portion 2 of the present embodiment may be a V-shaped needle portion that is configured only by the side wall portions 13*a* and 13*b* and has a substantially V-shaped outer shape in a cross-sectional view orthogonal to the longitudinal direction A.

In addition, the thicknesses of the side wall portions 13*a* and 13*b* and the bottom portion 13*c* of the puncture portion 2 of the present embodiment are substantially uniform, but the present invention is not limited to this configuration. The thicknesses of the side wall portions 13*a* and 13*b* and the bottom portion 13*c* may be different from each other.

Furthermore, the outer diameter T1 (see FIG. 11) of the puncture portion 2 of the present embodiment is substantially constant on the proximal-end side from the distal-end surface on which the blade surface 2*a* is formed. That is, the puncture portion 2 of the present embodiment is configured to have a substantially uniform thickness in the longitudinal direction A except for the distal-end surface on which the blade surface 2*a* is formed. However, the outer diameter T1 of the puncture portion 2 may gradually decrease from the proximal-end side toward the distal end in the longitudinal direction A, for example.

<Retained Portion 3>

As shown in FIG. 1 and the like, the retained portion 3 of the present embodiment includes the tubular portion 11 and the tapered portion 12 described above. That is, as shown in FIGS. 9, 10, and the like, the distal end of the tapered portion 12 of the present embodiment is continuous with the proximal end of the puncture portion 2. The proximal end of the tapered portion 12 of the present embodiment is continuous with the distal end of the tubular portion 11. In addition, the proximal end surface of the puncture needle 1 of the present embodiment is formed of the proximal end surface of the tubular portion 11. The proximal end surface of the tubular portion 11 of the present embodiment is formed of a plane orthogonal to the longitudinal direction A.

As described above, the outer diameter T2 of the tubular portion 11 is substantially constant in the longitudinal direction A. Furthermore, the inner diameter of the tubular portion 11 of the present embodiment is substantially constant in the longitudinal direction A. As shown in FIG. 13, the tubular portion 11 of the present embodiment has a substantially uniform wall thickness over the entire region in the circumferential direction B around the central axis O. However, the wall thickness of the tubular portion 11 may be different depending on the position in the circumferential direction B.

As described above, the outer diameter T3 of the tapered portion 12 gradually decreases from the proximal-end side toward the distal end in the longitudinal direction A Furthermore, the inner diameter of the tapered portion 12 of the present embodiment also gradually decreases from the distal-end side toward the proximal end in the longitudinal direction A. As shown in FIG. 12, the tapered portion 12 of the present embodiment has a substantially uniform wall thickness regardless of the position in the circumferential direction B. However, the thickness of the tapered portion 12 may be different depending on the position in the circumferential direction B.

As described above, the width W of the slit 2*b* of the present embodiment gradually decreases toward the proximal end in the tapered portion 12. More specifically, as shown in FIG. 9, etc., the width W of the slit 2*b* of the present embodiment starts to gradually decrease from the position of the distal end of the tapered portion 12 and terminates at the position of the proximal end of the tapered portion 12. However, the position where the width W of the slit 2*b* starts to gradually decrease is not limited to the position of the distal end of the tapered portion 12. The slit 2*b* may start to gradually decrease on the proximal-end side relative to the position of the distal end of the tapered portion 12. The position where the slit 2*b* terminates is not limited to the position of the proximal end of the tapered portion 12. The slit 2*b* may terminate on the distal-end side relative to the position of the proximal end of the tapered portion 12.

<Shapes of Contour Lines of Puncture Portion 2 and Retained Portion 3>

Next, the shapes of the contour lines of the puncture portion 2 and the retained portion 3 when the puncture needle 1 of the present embodiment is viewed from a predetermined viewpoint will be described.

As described above, in a lateral view in which the slit 2*b* of the puncture portion 2 faces upward (see FIGS. 5, 6, and 10), a lower contour line CL1 of the puncture portion 2, a lower contour line CL2 of the tubular portion 11, and a lower contour line CL3 of the tapered portion 12 are linearly connected. In addition, in the present embodiment, in a lateral view in which the slit 2*b* of the puncture portion 2 faces upward (see FIGS. 5, 6, and 10), the contour lines linearly connected on the lower puncture-portion side 2, the tubular portion 11, and the tapered portion 12 extends parallel to the longitudinal direction A (or the central axis O). The distal-end side of the contour lines linearly connected terminates at the position of the needle tip 4. Further, the proximal-end side of the contour lines linearly connected terminates at the position of the proximal end of the tubular portion 11.

On the other hand, in the present embodiment, in a lateral view in which the slit 2*b* of the puncture portion 2 faces upward (see FIGS. 5, 6, and 10), an upper contour line CL4 of the puncture portion 2, an upper contour line CL5 of the tubular portion 11, and an upper contour line CL6 of the tapered portion 12 are not linearly connected.

Specifically, in a lateral view in which the slit 2*b* of the puncture portion 2 faces upward (see FIGS. 5, 6, and 10), the upper contour line CL4 of the puncture portion 2 and the upper contour line CL6 of the tapered portion 12 are connected at an angle. More specifically, in a lateral view in which the slit 2*b* of the puncture portion 2 faces upward (see FIGS. 5, 6, and 10), the upper contour line CL4 of the puncture portion 2 is a straight line extending in parallel with the longitudinal direction A. On the other hand, in a lateral view in which the slit 2*b* of the puncture portion 2 faces upward (see FIGS. 5, 6, and 10), the upper contour line CL6 of the tapered portion 12 is a straight line extending obliquely with respect to the longitudinal direction A in a manner of approaching the lower contour line CL3 from the proximal-end side toward the distal end.

In a lateral view in which the slit 2*b* of the puncture portion 2 faces upward (see FIGS. 5, 6, and 10), the upper contour line CL5 of the tubular portion 11 and the upper contour line CL6 of the tapered portion 12 are connected at an angle. More specifically, in a lateral view in which the slit 2*b* of the puncture portion 2 faces upward (see FIGS. 5, 6, and 10), the upper contour line CL5 of the tubular portion 11 is a straight line extending in parallel with the longitudinal direction A. On the other hand, in a lateral view in which the slit 2*b* of the puncture portion 2 faces upward (see FIGS. 5, 6, and 10), the upper contour line CL6 of the tapered portion 12 is a straight line extending obliquely with respect to the longitudinal direction A in a manner of approaching the lower contour line CL3 from the proximal-end side toward the distal end as described above. In a lateral view of the puncture needle 1, the contour line CL6 of the taper 12 is inclined with respect to the central axis O of the tubular portion 11.

Furthermore, in a lateral view in which the slit 2*b* of the puncture portion 2 faces upward (see FIGS. 5, 6, and 10), both the upper contour line CL4 of the puncture portion 2 and the upper contour line CL5 of the tubular portion 11 are straight lines parallel to the longitudinal direction A, but the upper and lower positions are different in the lateral view, and are not positioned on the same straight line. More specifically, in a lateral view in which the slit 2*b* of the puncture portion 2 faces upward (see FIGS. 5, 6, and 10), the upper contour line CL5 of the tubular portion 11 is positioned above the upper contour line CL4 of the puncture portion 2.

In other words, as shown in FIG. 10, in a lateral view in which the slit 2*b* of the puncture portion 2 faces upward, a distance H1 in the height direction between the lower contour line CL1 and the upper contour line CL4 of the puncture portion 2 is shorter than a distance H2 in the height direction between the lower contour line CL2 and the upper contour line CL5 of the tubular portion 11. In the present embodiment, the aforementioned distance H1 is longer than ½ of the aforementioned distance H2.

As described above, in the puncture needle 1 of the present embodiment, in a lateral view in which the slit 2*b* of the puncture portion 2 faces upward (see FIGS. 5, 6, and 10), the lower contour lines of the puncture portion 2, the tubular portion 11, and the tapered portion 12 are linearly connected, whereas the upper contour lines of the puncture portion 2, the tubular portion 11, and the tapered portion 12 are not linearly connected.

Next, the contour lines of the puncture portion 2 and the retained portion 3 in a top view (see FIGS. 3 and 9) when the puncture needle 1 is viewed from the slit 2*b* side will be described. The shape of the contour lines of the puncture portion 2 and the retained portion 3 in the bottom view of the puncture needle 1 from the opposite side of the slit 2*b* (see FIG. 4) is the same as in the top view (see FIGS. 3 and 9) and therefore the description is omitted.

In a top view (see FIGS. 3 and 9), the center positions of the puncture portion 2, the tubular portion 11, and the tapered portion 12 in a width direction C orthogonal to the longitudinal direction A are aligned. That is, in a top view (see FIGS. 3 and 9), a center straight line passing through the center position in the width direction C of the puncture portion 2, a center straight line passing through the center position in the width direction C of the tubular portion 11, and a center straight line passing through the center position in the width direction C of the tapered portion 12 are common. In the present embodiment, hereinafter, for convenience of description, the common center straight line is referred to as a "common center line M." The common center straight line M of the present embodiment extends parallel to the longitudinal direction A.

In addition, in the present embodiment, the contour lines of the puncture portion 2, the tubular portion 11, and the tapered portion 12 located on both sides in the width direction C are arranged symmetrically with respect to the above-described common center straight line M in a top view (see FIGS. 3 and 9).

Furthermore, in the present embodiment, in a top view (see FIGS. 3 and 9), a contour line CL7 on one side in the width direction C of the puncture portion 2, a contour line CL8 on one side in the width direction C of the tubular portion 11, and a contour line CL9 on one side in the width direction C of the tapered portion 12 are not linearly connected. In addition, in a top view (See FIGS. 3 and 9), a contour line CL10 on the other side in the width direction C of the puncture portion 2, a contour line CL11 on the other side in the width direction C of the tubular portion 11, and a contour line CL12 on the other side in the width direction C of the tapered portion 12 are not linearly connected.

Specifically, in a top view (see FIGS. 3 and 9), the contour line CL7 on one side in the width direction C of the puncture portion 2 and the contour line CL9 on one side in the width direction C of the tapered portion 12 are connected at an angle. More specifically, in a top view (see FIGS. 3 and 9), the contour line CL7 on one side in the width direction C of the puncture portion 2 is a straight line extending in parallel with the longitudinal direction A. On the other hand, in a top view (see FIGS. 3 and 9), the contour line CL9 on one side in the width direction C of the tapered portion 12 is a straight line extending obliquely with respect to the longitudinal direction A in a manner of approaching the common center straight line M from the proximal-end side toward the distal end.

In a top view (see FIGS. 3 and 9), the contour line CL8 on one side in the width direction C of the tubular portion 11 and the contour line CL9 on one side in the width direction C of the tapered portion 12 are continuous at an angle. More specifically, in a top view (see FIGS. 3 and 9), the contour line CL8 on one side in the width direction C of the tubular portion 11 is a straight line extending parallel to the longitudinal direction A. On the other hand, in a top view (see FIGS. 3 and 9), the contour line CL9 on one side in the width direction C of the tapered portion 12 is a straight line extending obliquely with respect to the longitudinal direction A in a manner of approaching the common center straight line M from the proximal-end side toward the distal end as described above.

Furthermore, in a top view (see FIGS. 3 and 9), the contour line CL7 on one side in the width direction C of the puncture portion 2 and the contour line CL8 on one side in the width direction C of the tubular portion 11 are both straight lines parallel to the longitudinal direction A, but the positions where the respective contour lines extend are different in the top view, and are not positioned on the same straight line. More specifically, in a top view (see FIGS. 3 and 9), the contour line CL8 on one side in the width direction C of the tubular portion 11 is at a position farther from the common center straight line M in the width direction C than the contour line CL7 on one side in the width direction C of the puncture portion 2. In other words, as shown in FIG. 9, in top view, a distance H3 in the width direction C between the contour lines CL7 and CL10 on both sides of the puncture portion 2 is shorter than a distance H4 in the width direction C between the contour lines CL8 and CL11 on both sides of the tubular portion 11. In the present embodiment, the aforementioned distance H3 is longer than ½ of the above-described distance H4.

The relationship between the contour line CL10 on the other side in the width direction C of the puncture portion 2, the contour line CL11 on the other side in the width direction C of the tubular portion 11, and the contour line CL12 on the other side in the width direction C of the tapered portion 12 in a top view (see FIGS. 3 and 9) is also the same as the relationship between the contour line CL7 on one side in the width direction C of the puncture portion 2, the contour line CL8 on one side in the width direction C of the tubular portion 11, and the contour line CL9 on one side in the width direction C of the tapered portion 12 described above, and thus the description thereof is omitted here.

Here, an inclination angle with respect to the longitudinal direction A of the upper contour line CL6 of the tapered portion 12 shown in FIG. 10 is θ1. θ1 is preferably 0.5° or more and 60° or less, and more preferably 3° or more and 10° or less. Within this range, it is possible to sufficiently secure the attachment to the hub and the adhesive application amount to be described later, and it is possible to prevent detachment of the puncture needle from the hub. An inclination angle of the contour line CL9 on one side and the contour line CL12 on the other side in the width direction C of the tapered portion 12 with respect to the longitudinal direction A shown in FIG. 9 is θ2. In the present embodiment, θ1 is larger than θ2.

[Method for Manufacturing Puncture Needle]

Figure 20:
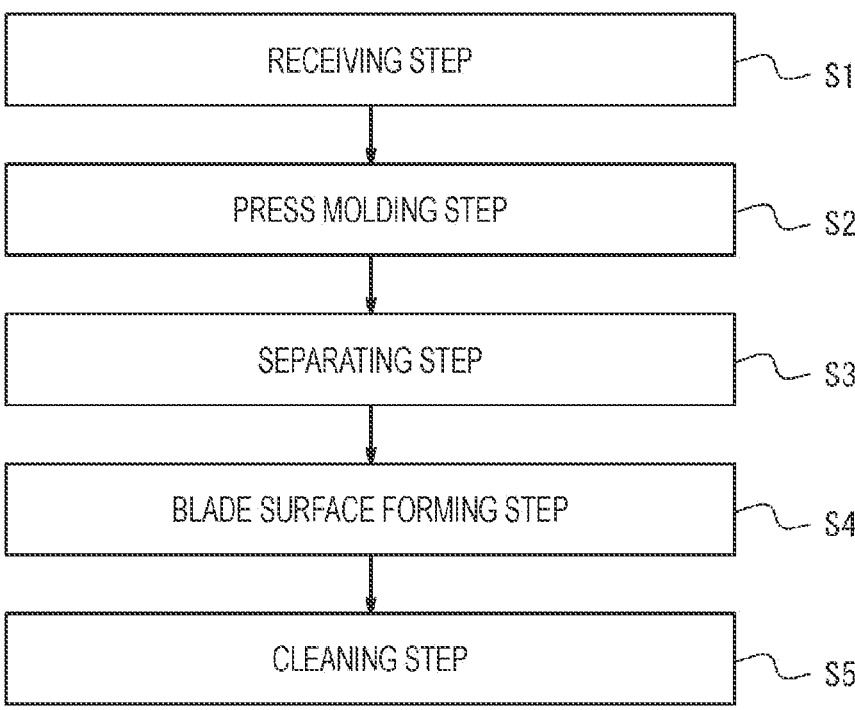
FIG. 20 is a diagram showing a manufacturing flow of the puncture needle of the present disclosure.
Figure 23:
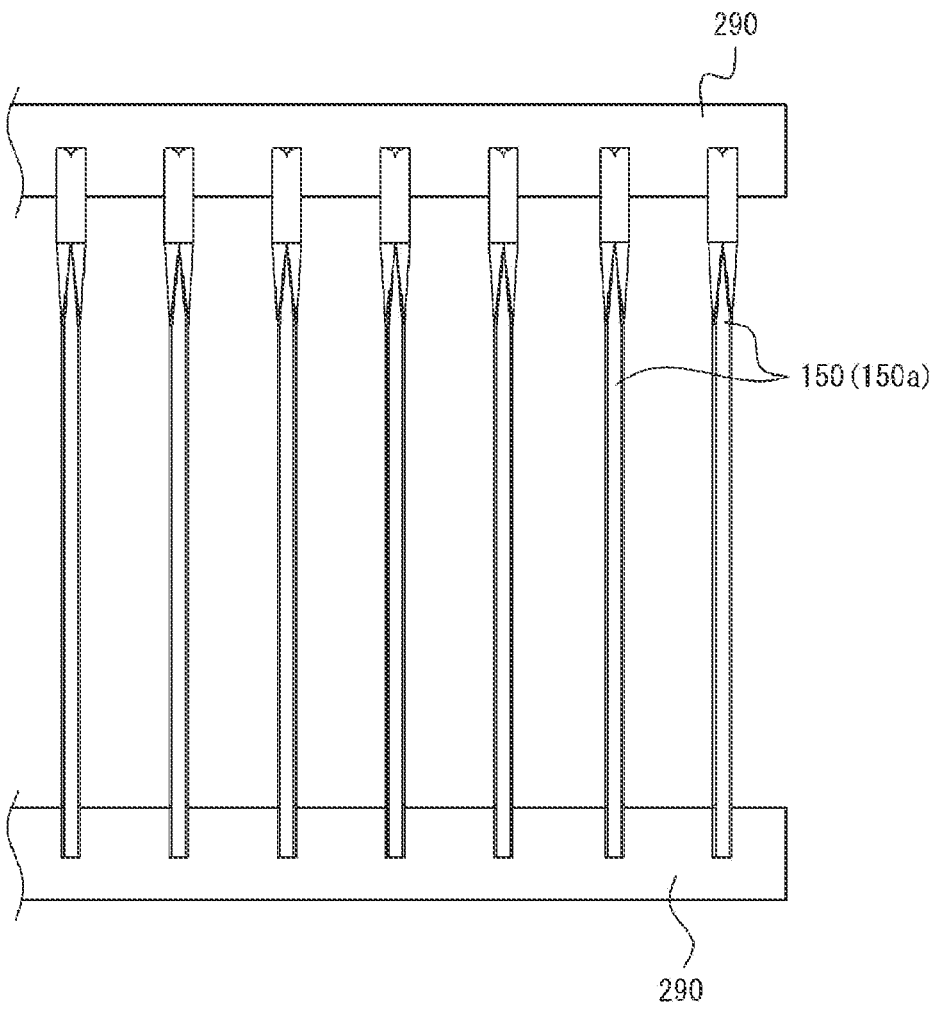
FIG. 23 is a view showing an example of a separating step shown in FIG. 20.

As shown in FIG. 20, the method for manufacturing the puncture needle 1 includes: receiving step S1 of receiving a strip-shaped metal plate material in a press molding machine; press molding step S2 of continuously press molding the plate material by the press molding machine to obtain a plurality of bar-shaped members 150 (see FIG. 23) partially connected to the plate material; separating step S3 of separating the bar-shaped member 150 from the plate material; blade surface forming step S4 of forming a blade surface at one end of the bar-shaped member 150 to form the blade surface; and cleaning step S5 of cleaning the bar-shaped member 150.

<Receiving Step S1>

A strip-shaped metal plate material is received in a press molding machine (not shown). In this case, the plate material is moved in the longitudinal direction thereof with respect to the press molding machine by a moving mechanism, and the molding location of the plate material is positioned at the molding position of the press molding machine. First, a portion of the plate material from which a predetermined developed shape body is punched out is placed at a position of the punching portion of the press molding machine to be described below, where the developed shape body is punched out.

<Press Molding Step S2>

Figure 21:
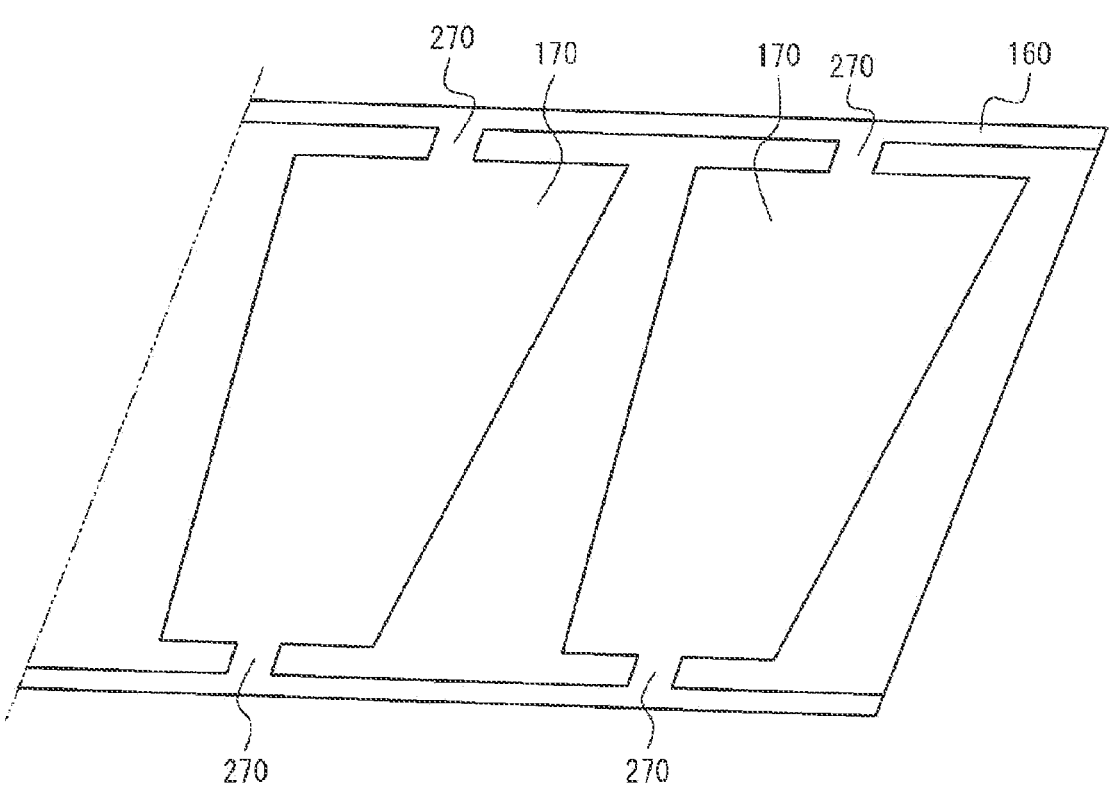
FIG. 21 is a view showing a first step of the press molding step shown in FIG. 20.
Figure 22:
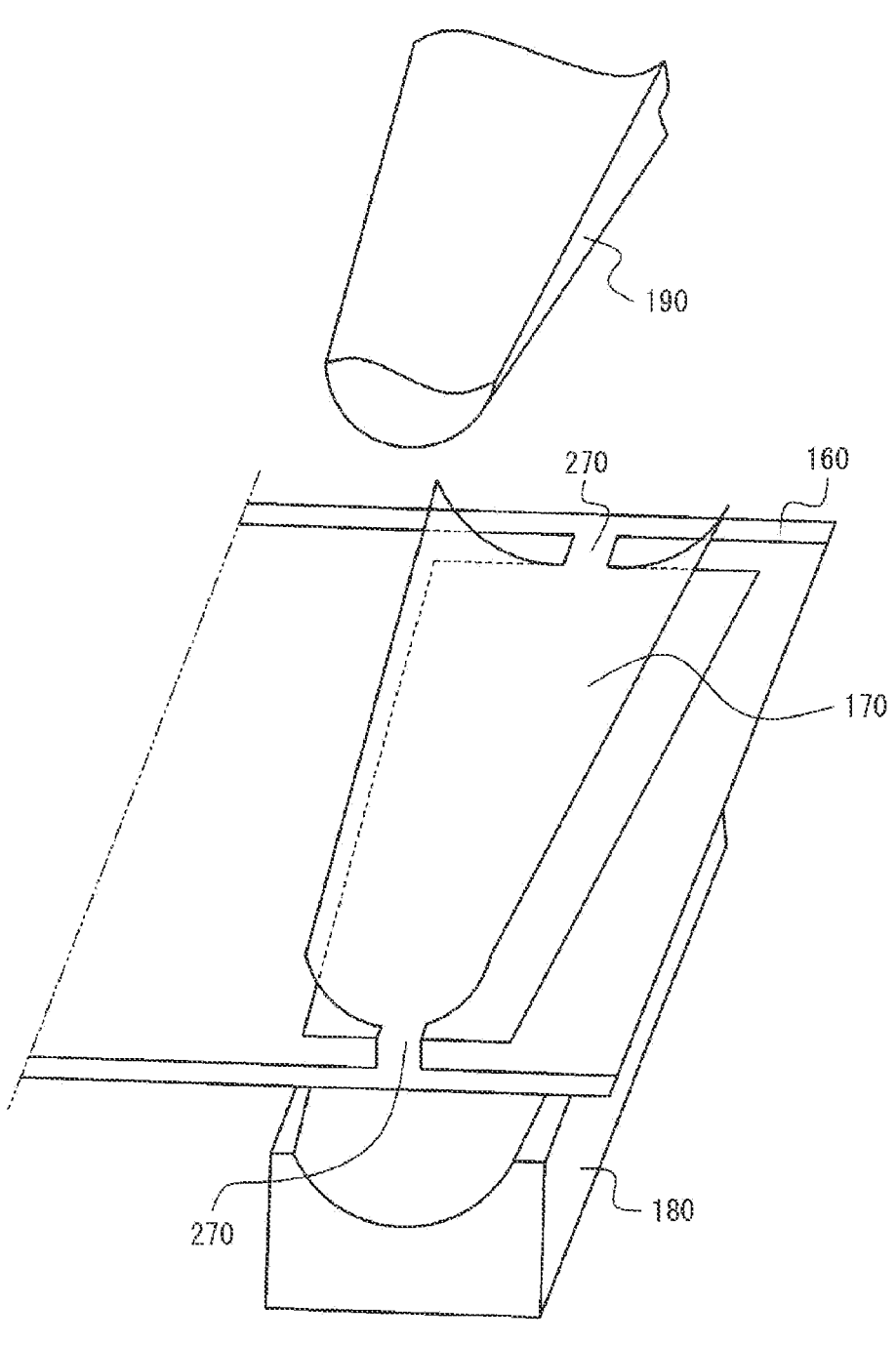
FIG. 22 is a view showing a second step of the press molding step shown in FIG. 20.

Press molding step S2 is a step of obtaining the bar-shaped member 150 (see FIG. 23) from a plate material 160 by the press molding machine. Here, the bar-shaped member 150 is substantially equivalent to the puncture needle 1 having no blade surface 2a, and includes a slit 2b (see FIG. 1), a tapered portion 12 (see FIG. 1), and a tubular portion 11 (see FIG. 1). Press molding step S2 includes a first step (see FIG. 21) of punching a developed shape body having a shape in which the bar-shaped member 150 is developed into a plate material in a state where the developed shape body is partially connected to the plate material, and a second step (see FIG. 22) of using the press molding machine to bend the developed shape body at least once by a convex die and a concave die to mold the curved body into a tubular shape to obtain the bar-shaped member 150 in a state where the developed shape body is partially connected to the plate material. In the second step, using a continuous press molding machine, the developed shape body 170 is continuously press molded with a plurality of concave dies (molds) 180 and convex dies (molds) 190 to form the bar-shaped member 150 corresponding to the puncture needle 1, except for the blade surface 2a. Surface processing, such as knurling, on the outer surface of the bar-shaped member 150 is performed in the press forming step.

<Separating Step S3>

In separating step S3, the bar-shaped member 150 is sequentially separated from the plate material 160 on the frame. In this case, the bar-shaped member 150 is separated at the boundary between the bar-shaped member 150 and a pair of connection portions 270. The method for separating the bar-shaped member from the plate material 160 is not particularly limited, and for example, the bar-shaped member 150 may be mechanically cut or separated using a laser or the like. In addition, in separating step S3, substantially at the same time as the separation of the bar-shaped member 150 or after the separation of the bar-shaped member 150, each bar-shaped member 150 is temporarily fixed, and the positional relationship between the bar-shaped members 150 is maintained. In the present embodiment, the temporary fixing is performed by bonding both end portions of the bar-shaped member 150 to a pair of adhesive tapes (temporary fixing members) 290 (see FIG. 23), or bonding at least one portion of the bar-shaped member 150 excluding the central portion in the longitudinal direction to the adhesive tape 290.

<Blade Surface Forming Step S4>

In the blade surface forming step, the blade surface 2a is formed on at least one end portion of each of temporarily fixed bar-shaped members 150a to form the puncture needle 1. Because the bar-shaped member 150 has the contour lines CL1, CL2, and CL3 (see FIG. 5, etc.) linearly connected, the puncture needle 1 can be accurately supported by the temporary fixing jig. Thus, the blade surface 2a can be formed while accurately defining the position of the blade surface 2a with respect to the slit 2b.

In the present disclosure, the slit 2b is formed in advance in press molding step S2, but it is also possible to form a normally closed tube in press molding step S2 and form the blade surface and the slit in blade surface forming step S4. However, because the slit 2b has a significantly larger area to be ground than the blade surface 2a, in a case in which the blade surface and the slit 2b are formed in blade surface forming step S4, mass productivity is significantly deteriorated. Therefore, in the present disclosure, a manufacturing step of forming the slit 2b in press molding step S2 and then forming the blade surface 2a in blade surface forming step S4 is adopted. Then, in blade surface forming step S4, in order to form the blade surface 2a at a constant position with respect to the slit 2b, contour lines CL1, CL2, and CL3 (see FIG. 5, etc.) linearly connected are provided in the bar-shaped member 150 (puncture needle 1).

<Cleaning Step S5>

In cleaning step S5, the metal piece or the like attached to the puncture needle 1 is removed in blade surface forming step S4 or the like. As the cleaning method, a known method can be employed.

Note that, in the manufacturing step of the puncture needle 1, a correcting step, a polishing step, a joining step, and the like can be incorporated as necessary.

[Needle Assembly]

Figure 14:
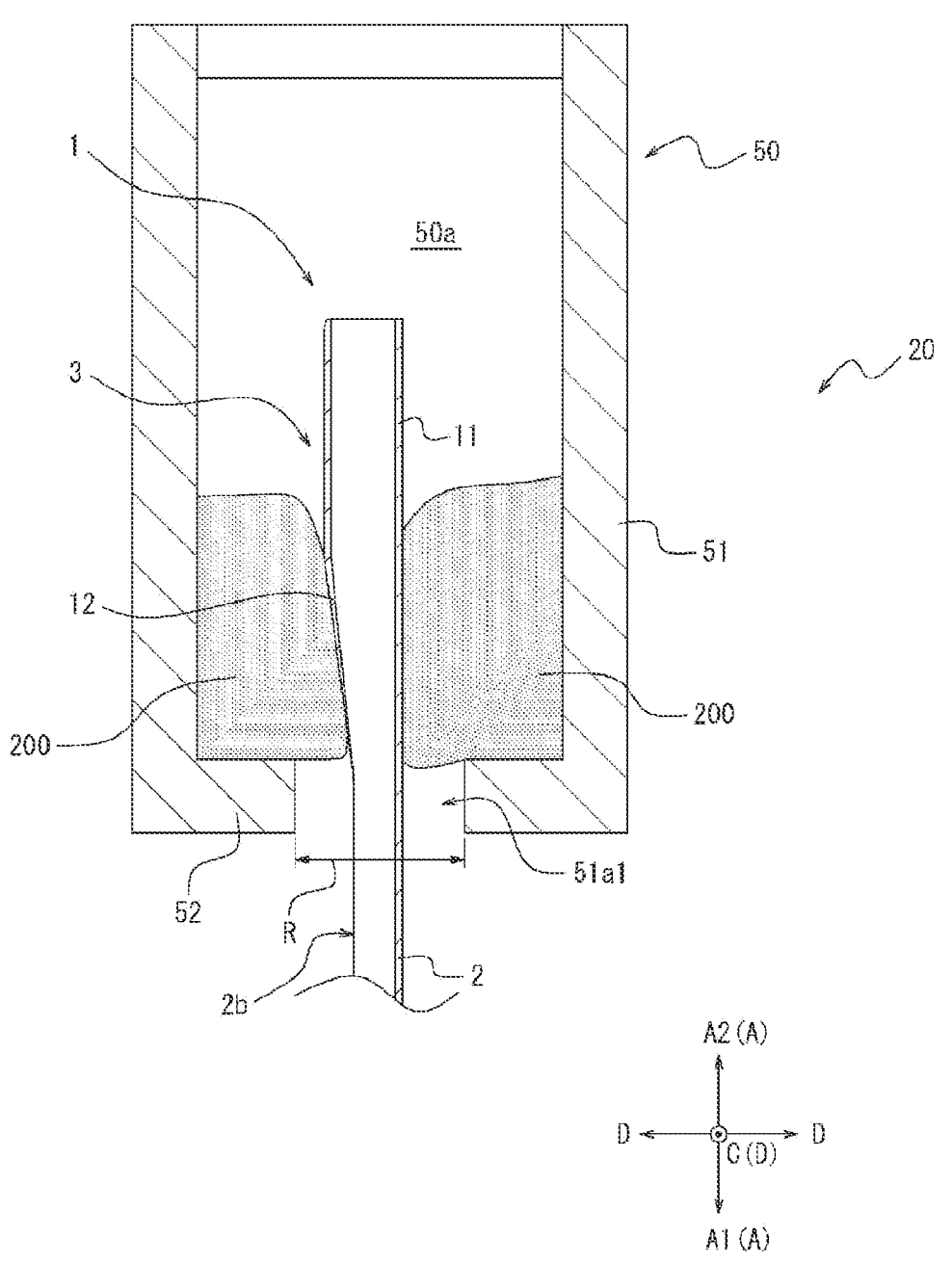
FIG. 14 is a cross-sectional view of a needle assembly as one embodiment of the present disclosure including the puncture needle shown in FIG. 1, taken along line IV-IV in FIG. 9.
Figure 15:
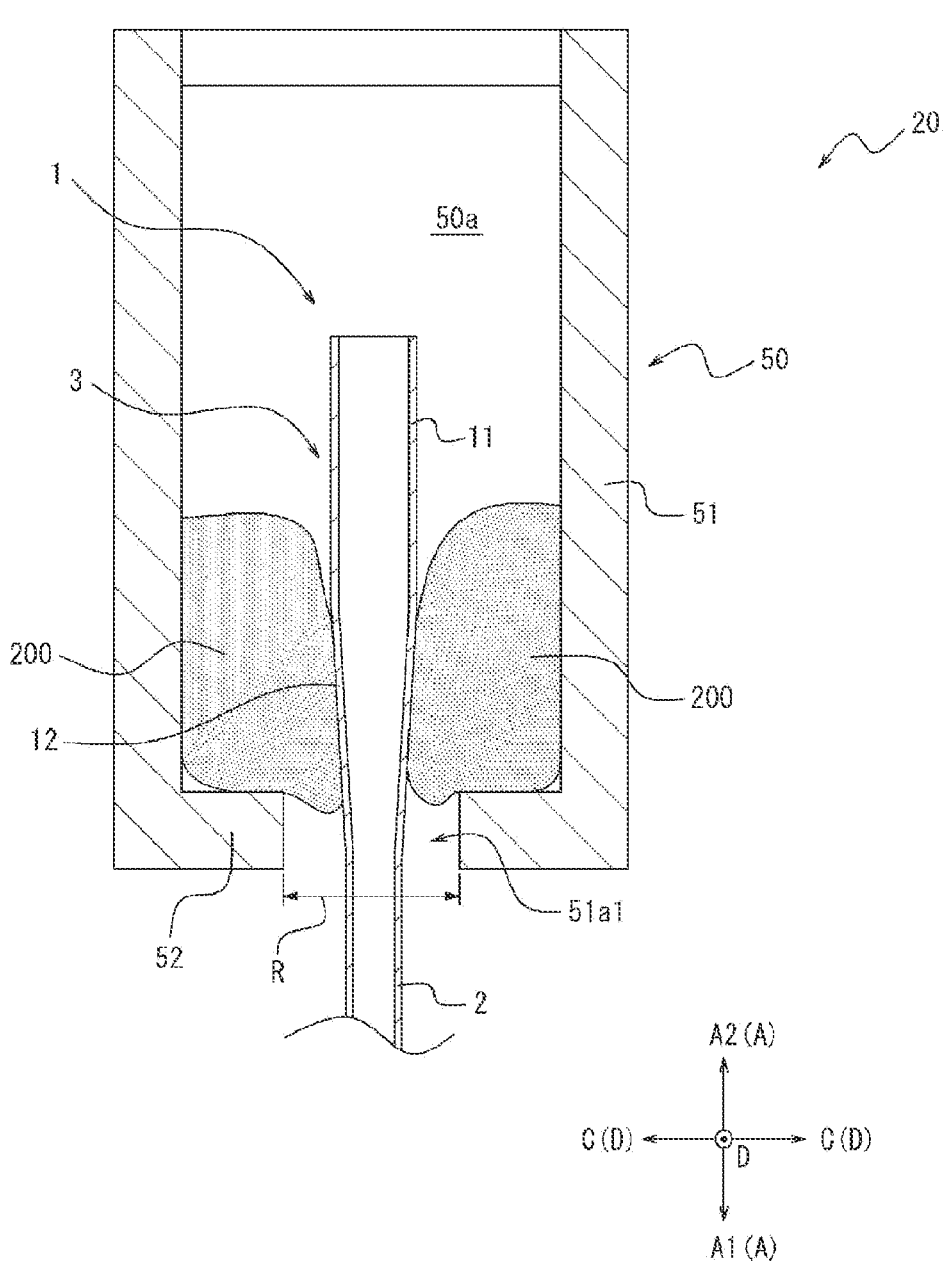
FIG. 15 is a cross-sectional view of the needle assembly shown in FIG. 14, taken along line V-V in FIG. 10.

Next, the needle assembly 20 as one embodiment of the needle assembly according to the present disclosure will be described by way of example with reference to FIGS. 14 and 15. The needle assembly 20 includes, as described above, the puncture needle 1 and the hub 50 that retains the retained portion 3 of the puncture needle 1. FIGS. 14 and 15 are views showing the needle assembly 20. Specifically, FIGS. 14 and 15 are cross-sectional views of the needle assembly 20 showing a state in which the retained portion 3 of the puncture needle 1 is retained by the hub 50. FIG. 14 shows a cross section of the puncture needle 1 taken along line IV-IV in FIG. 9. In addition, FIG. 15 shows a cross section of the puncture needle 1 taken along line V-V in FIG. 10.

As shown in FIGS. 14 and 15, the hub 50 includes a surrounding wall portion 51 that defines an accommodation space 50a capable of accommodating the retained portion 3 of the puncture needle 1. As shown in FIGS. 14 and 15, the puncture needle 1 is retained by the hub 50 in a state where the retained portion 3 is accommodated in the accommodation space 50a in the surrounding wall portion 51 and the puncture portion 2 protrudes from the opening 51a1 on one side (lower side in FIGS. 14 and 15) of the surrounding wall portion 51.

More specifically, the needle assembly 20 of the present embodiment includes an adhesive member 200 that bonds the outer surface of the tapered portion 12 of the retained portion 3 of the puncture needle 1 and the inner surface of the surrounding wall portion 51. The adhesive member 200 may be, for example, an adhesive that is filled and solidified in the surrounding wall portion 51. The adhesive as the adhesive member 200 is filled in a manner of being in contact with the outer surface of the tapered portion 12 inclined with respect to the longitudinal direction A, and is solidified in that state. As a result, it is possible to prevent the tapered portion 12 from being caught by the adhesive as the adhesive member 200 and the retained portion 3 of the puncture needle 1 from falling off the hub 50 in the insertion direction A1. That is, providing the tapered portion 12 in the retained portion 3 of the puncture needle 1 can improve the joint strength of the puncture needle 1 to the hub 50. In a case in which the adhesive member 200 is applied at least on the tapered portion 12, the hub 50 and the puncture needle 1 can be reliably joined.

As shown in FIGS. 14 and 15, the hub 50 of the needle assembly 20 shown in the present embodiment includes the surrounding wall portion 51 and the wall end surface 52. The opening 51a1 is defined by the inner edge of the wall end surface 52. The opening 51a1 of the present embodiment is a circular opening, whose shape is not particularly limited.

In addition, as shown in FIGS. 14 and 15, a minimum diameter R of the opening 51a1 of the present embodiment is substantially the same as the outer diameter T2 of the tubular portion 11 of the puncture needle 1 or slightly larger than the outer diameter T2 of the tubular portion 11 of the puncture needle 1. Therefore, in the present embodiment, at least the periphery of the tapered portion 12 of the retained portion 3 is filled with the adhesive as the adhesive member 200, so that removal from the hub 50 through the opening 51a1 of the retained portion 3 is suppressed. In this manner, by filling the periphery of the tapered portion 12 with the adhesive member 200, the retention property of the adhesive member 200 in the accommodation space 50a can be enhanced. However, the minimum diameter R of the opening 51a1 may be smaller than the outer diameter T2 of the tubular portion 11. Providing the wall end surface 52 having such an opening 51a1 makes it possible to suppress detachment of the puncture needle 1 from the hub 50.

The shape of the hub 50 shown in the present embodiment is an example, and the shape is not particularly limited as long as the retained portion 3 of the puncture needle 1 is retained. Therefore, it may have a shape like the hub 50 shown in FIGS. 16 to 19 to be referred to later.

Examples of the material of the hub 50 include a resin material. Examples of the resin material include thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluororesin, polycarbonate, polyamide, acetal resin, acrylic resin, and polyethylene terephthalate, and thermosetting resins such as phenol resin, epoxy resin, silicone resin, and unsaturated polyester. As the adhesive member 200, any adhesive such as a UV curable resin may be used.

[Puncture Tool 100]

Next, with reference to FIGS. 16 to 19, the views show the puncture tool 100 including the needle assembly 20 having the puncture needle 1 and the hub 50. The shape of the hub 50 shown in FIGS. 16 to 19 is different from the shape of the hub 50 shown in FIGS. 14 and 15 described above, but may have a similar shape. The shape of the hub 50 may be appropriately designed according to the configuration of the puncture tool 100 to which the needle assembly 20 is applied.

Figure 16:
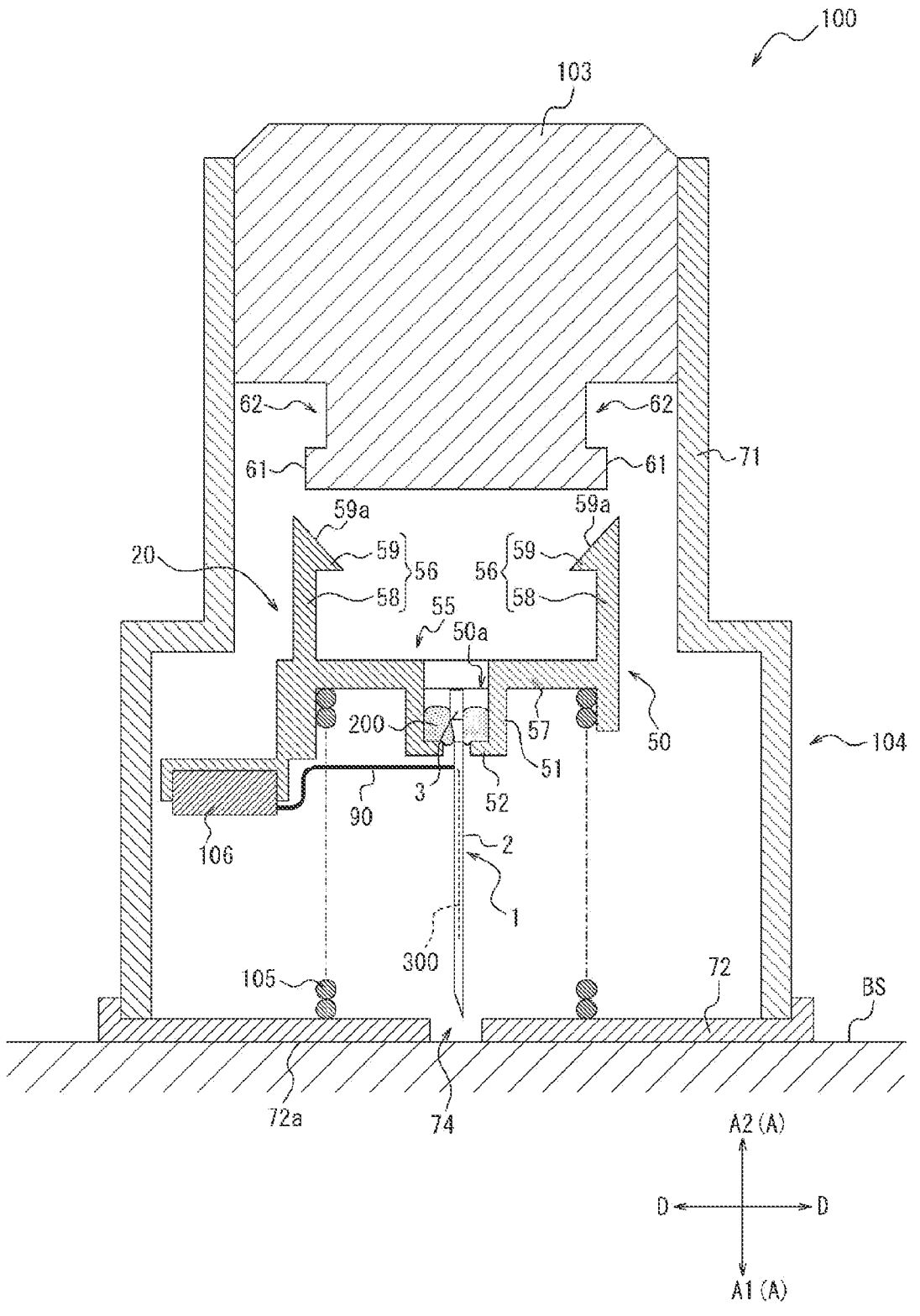
FIG. 16 is a view showing a puncture tool including the needle assembly shown in FIG. 14, and shows a state in which the puncture needle is in a standby position.
Figure 17:
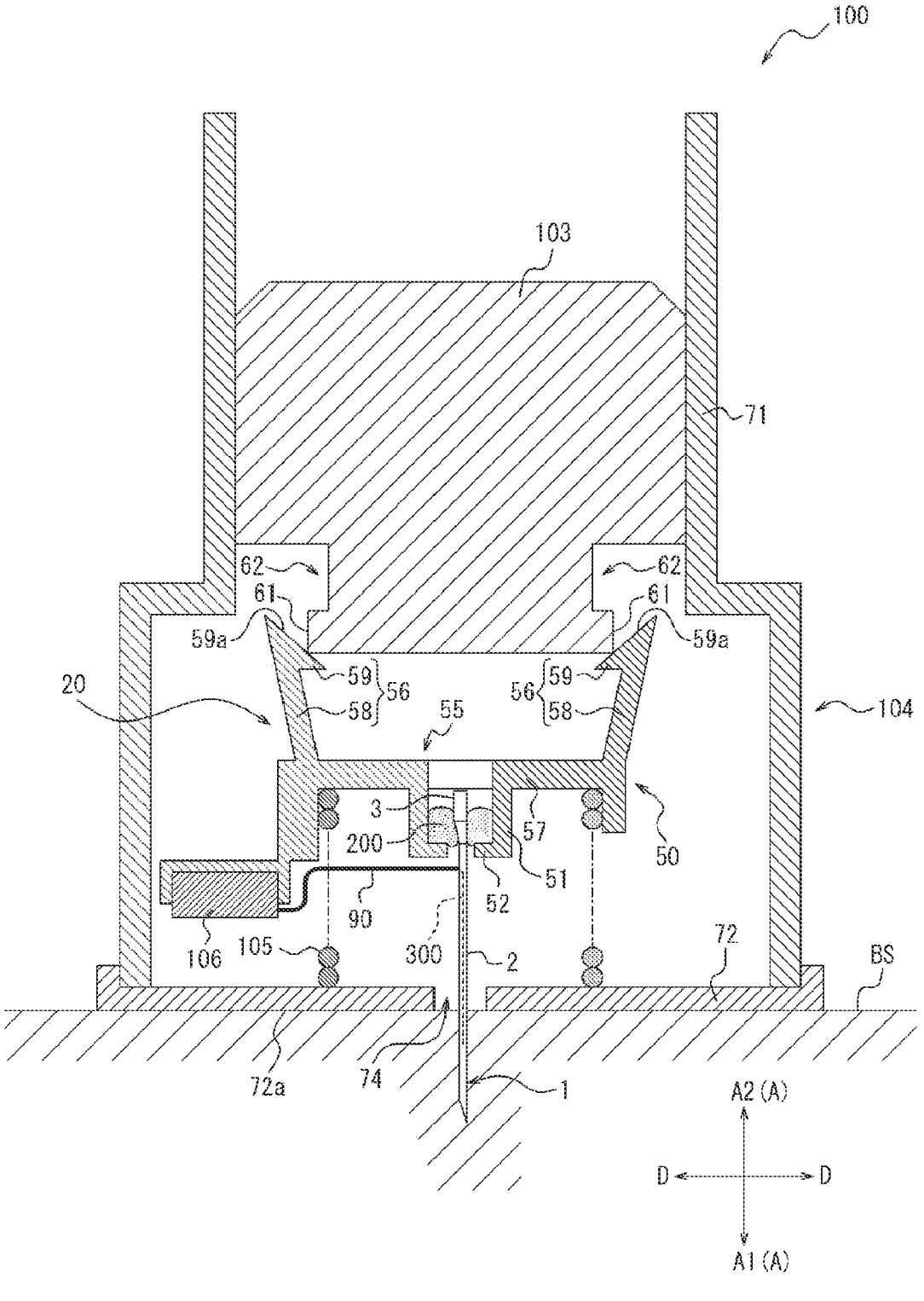
FIG. 17 is a view showing a state in which the puncture needle of the puncture tool shown in FIG. 16 is moving from the standby position to an insertion position.
Figure 18:
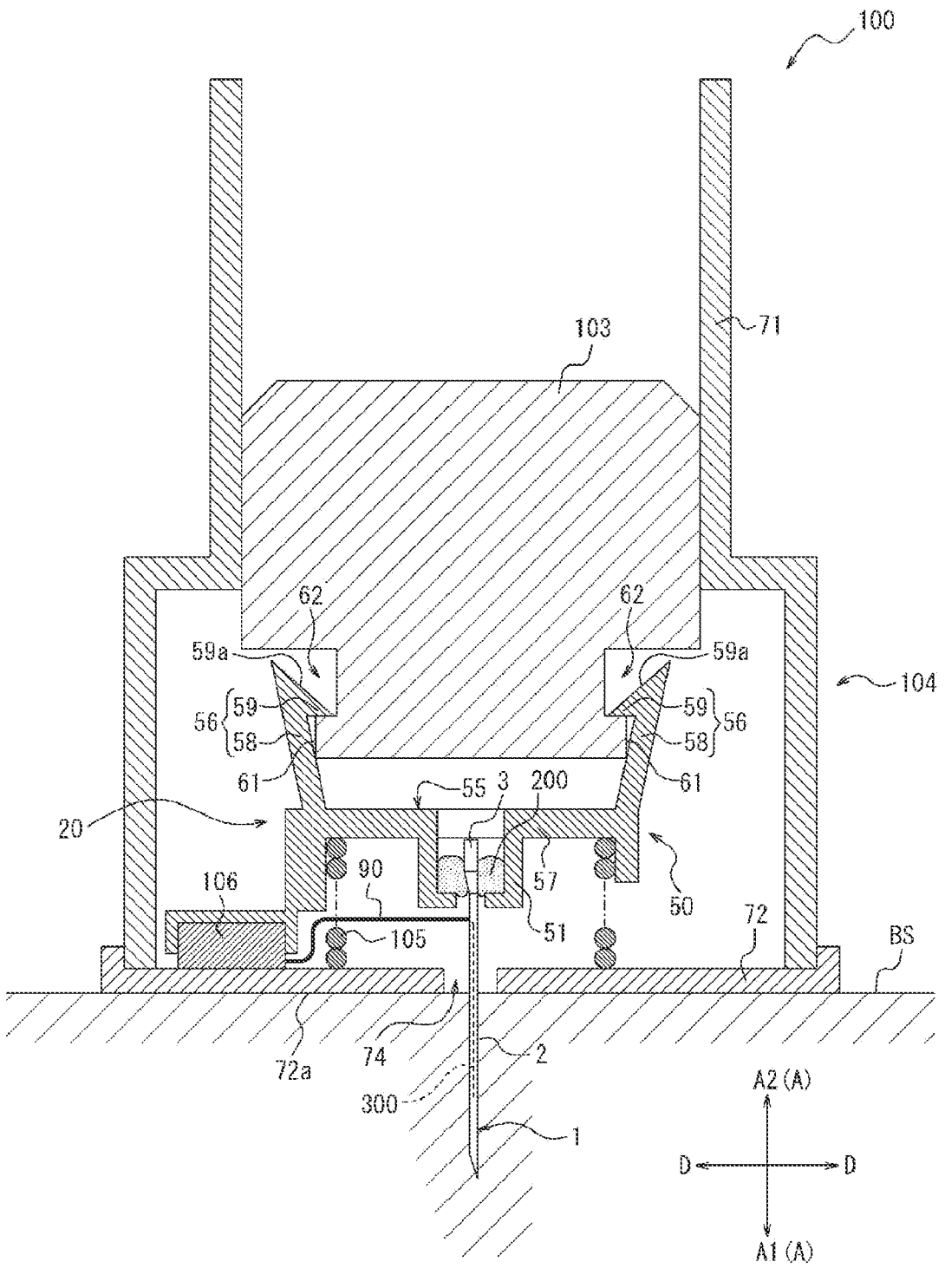
FIG. 18 is a view showing a state in which the puncture needle of the puncture tool shown in FIG. 16 is at the insertion position.
Figure 19:
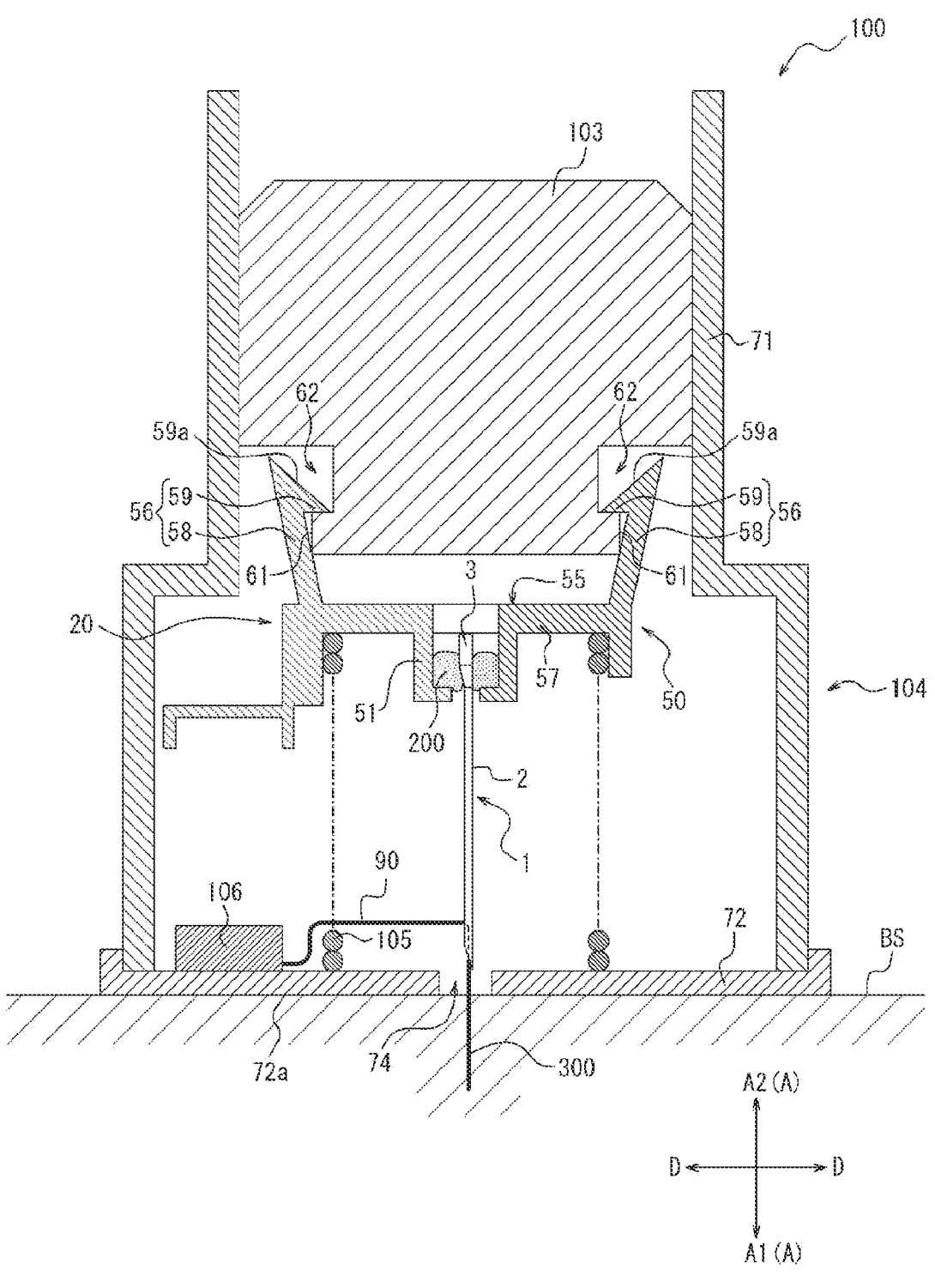
FIG. 19 is a view showing a state in which the puncture needle of the puncture tool shown in FIG. 16 is removed from the insertion position to an outside of a living body.

FIGS. 16 to 19 are views showing the puncture tool 100. FIGS. 16 to 19 each show an outline of the operation of the puncture tool 100 when the sensor 300 is inserted and indwelled in the living body using the puncture tool 100. Specifically, FIG. 16 shows a state in which the puncture needle 1 is in a standby position. FIG. 17 shows a state in which the puncture needle 1 is moving from the standby position to an insertion position. FIG. 18 shows a state in which the puncture needle 1 is at the insertion position. FIG. 19 shows a state in which the puncture needle 1 has been removed from the insertion position to the outside of the living body.

As shown in FIGS. 16 to 19, the puncture tool 100 includes the needle assembly 20, a moving member 103, a housing 104, a biasing member 105, a detector 106, and a sensor 300. As shown in FIGS. 16 to 19, the needle assembly 20 of the present embodiment includes the puncture needle 1 and the hub 50.

First, a method of using the puncture tool 100 of the present embodiment will be described with reference to FIGS. 16 to 19. The puncture tool 100 of the present embodiment can be used to insert and indwell the sensor 300 into the living body as described above. The puncture tool 100 is arranged on a living body surface BS in the state shown in FIG. 16. That is, FIG. 16 shows a state before the puncture needle 1 of the needle assembly 20 and the sensor 300 are inserted into the living body. Thereafter, when an operator such as a patient operates the puncture tool 100, the puncture needle 1 of the needle assembly 20 and the sensor 300 are inserted into the living body (see FIGS. 17 and 18). FIG. 17 is a view showing a state in which the puncture needle 1 and the sensor 300 are being inserted into the living body by the puncture tool 100. FIG. 18 is a view showing a state in which the puncture needle 1 and the sensor 300 have reached the deepest position in the living body that can be inserted by the puncture tool 100. Next, as shown in FIG. 19, the puncture needle 1 of the needle assembly 20 is removed from the living body in a state where the sensor 300 remains in the living body. In this manner, the sensor 300 can be inserted and indwelled in the living body by the puncture tool 100. Hereinafter, for convenience of description, the position of the puncture needle 1 in FIG. 16 where the puncture needle 1 is accommodated in the housing 104 will be referred to as a "standby position of the puncture needle 1." Furthermore, for convenience of description, the position of the puncture needle 1 in FIG. 18 where the puncture needle 1 protrudes most from the housing 104 will be referred to as an "insertion position of the puncture needle 1."

The sensor 300 indwelled in the living body detects a substance to be measured (analyte) and transmits information of a detection result to the detector 106. The detector 106 is connected to the sensor 300 in a wired manner and is indwelled on the living body surface BS together with the sensor 300. The detector 106 includes a processor as a control unit, a memory as a storage unit, a battery as a power supply unit, and the like. The sensor 300 of the present embodiment shown in FIGS. 16 to 19 transmits information including a detection result to the detector 106. Using the sensor 300 together with the detector 106 makes it possible to detect a signal corresponding to the concentration of the substance to be measured. The detection signal is subject to signal processing and transmitted by the detector 106 to a smartphone or a dedicated terminal of a subject. The subject or the user can check the measurement result of the substance to be measured displayed on the screen of the smartphone or the dedicated terminal over time. The period during which the sensor 300 is worn by the subject is appropriately determined by the judgment of a doctor or the like, for example, several hours, several days, one week, one month, or the like. The substance to be measured is not particularly limited, but glucose, oxygen, pH, lactic acid, and the like in blood or interstitial fluid can be measured by selecting the sensing unit of the sensor 300. Note that the detector 106 is connected to a transmitter (not shown) provided separately after the sensor 300 is completely inserted. In this case, the transmitter, not the detector 106, may be configured to include a memory, a battery, or the like. Furthermore, the detector 106 indwelled with the sensor 300 may be a transmitter including a transmission device capable of transmitting information to an external device. That is, the transmitter may include a processor, a memory, a battery, and the like. The transmitter may be configured to be used for a longer period of time than the sensor 300. In addition, the detector 106 may be connected to the sensor 300 via the contact portion after the sensor 300 is indwelled by the puncture tool 100. In such a case, only the contact portion is previously indwelled on the living body surface BS by the puncture tool 100 together with the sensor 300, and then the detector 106 is connected to the contact portion.

Because the puncture needle 1 of the needle assembly 20 is similar to the above-described configuration, the description thereof is omitted here.

The hub 50 of the needle assembly 20 includes a main body portion 55 and a locking claw portion 56. The main body portion 55 includes the surrounding wall portion 51. The accommodation space 50a penetrating in the longitudinal direction A is defined in the surrounding wall portion 51. The retained portion 3 of the puncture needle 1 is fixed to the surrounding wall portion 51 of the main body portion 55 via an adhesive as the adhesive member 200 in a state of being inserted into the accommodation space 50a. The wall end surface 52 is connected to an end portion of the surrounding wall portion 51 on the insertion direction A1 side. In addition, the main body portion 55 of the present embodiment includes the outer flange portion 57 continuous with an end portion of the surrounding wall portion 51 on the removal direction A2 side. The locking claw portion 56 protrudes from the outer flange portion 57 of the main body portion 55 in the removal direction A2. Furthermore, in the needle assembly 20 of the present embodiment, a plurality of locking claw portions 56 is provided at a position on the periphery of the puncture needle 1 in a direction orthogonal to the longitudinal direction A of the puncture needle 1 so as to surround the periphery of the puncture needle 1. The locking claw portion 56 includes an extending portion 58 protruding from the main body portion 55 and an engaging protrusion portion 59 provided at an end portion of the extending portion 58 in the removal direction A2. The extending portion 58 is elastically deformable in a direction orthogonal to the longitudinal direction A with a position continuous with the main body portion 55 as a fulcrum. The engaging protrusion portion 59 protrudes from the end portion of the extending portion 58 in a direction orthogonal to the longitudinal direction A.

The moving member 103 of the present embodiment movably mounted in the housing 104 in the longitudinal direction A. The upper surface of the moving member 103 of the present embodiment in the removal direction A2 is exposed to the outside from the housing 104. Therefore, the operator of the puncture tool 100 can move the moving member 103 in the insertion direction A1 by pressing the moving member 103 exposed from the housing 104 in the insertion direction A1. As a result, the needle assembly 20 is pressed and moved in the insertion direction A1 by the moving member 103.

The moving member 103 includes an engaging portion 61 that presses the locking claw portion 56 of the hub 50 of the needle assembly 20 outward in a radial direction D of the puncture needle 1. The radial direction D of the puncture needle 1 means a radial direction of a circle around the central axis O of the tubular portion 11. In addition, the moving member 103 defines an engaging recess portion 62 into which the engaging protrusion portion 59 of the locking claw portion 56 can be fitted at a position adjacent to the engaging portion 61 in the removal direction A2. The engaging recess portion 62 is recessed inward in the radial direction D with respect to the engaging portion 61. As shown in FIGS. 16 to 19, the engaging portion 61 includes, for example, a disk portion. In addition, as shown in FIGS. 16 to 19, the engaging recess portion 62 is formed by, for example, an annular groove that is adjacent to the disk portion as the engaging portion 61 in the removal direction A2 and is recessed inward in the radial direction D relative to the outer edge of the disk portion. However, the configurations of the engaging portion 61 and the engaging recess portion 62 are not limited to the shapes and positions shown in the present embodiment.

As shown in FIGS. 16 to 18, the puncture tool 100 of the present embodiment can insert the puncture needle 1 and the sensor 300 into the living body by pushing the moving member 103 in the insertion direction A1. At this time, the engaging portion 61 of the moving member 103 is engaged with an inclined surface 59a located in the removal direction A2 of the engaging protrusion portion 59 of the locking claw portion 56, and presses the engaging protrusion portion 59 outward in the radial direction D. As a result, as shown in FIG. 17, the extending portion 58 of the locking claw portion 56 is elastically deformed outward in the radial direction D. That is, the plurality of locking claw portions 56 located on the outer periphery of the puncture needle 1 in the radial direction D is elastically deformed so as to be separated outward in the radial direction D. Therefore, as shown in FIG. 18, the engaging portion 61 of the moving member 103 can get over the engaging protrusion portion 59 in the insertion direction A1 while sliding on the inclined surface 59a of the engaging protrusion portion 59.

As shown in FIG. 18, when the engaging portion 61 of the moving member 103 gets over the engaging protrusion portion 59 of the hub 50 of the needle assembly 20, the engaging protrusion portion 59 is fitted into the engaging recess portion 62 of the moving member 103. As a result, the moving member 103 and the hub 50 of the needle assembly 20 interfere in the longitudinal direction A. That is, the needle assembly 20 and the moving member 103 are integrally movable in the longitudinal direction A. As a result, the needle assembly 20 and the moving member 103 can be integrated, and both can be moved in the removal direction A2.

Examples of the material of the moving member 103 include a resin material. Examples of the resin material include thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluororesin, polycarbonate, polyamide, acetal resin, acrylic resin, and polyethylene terephthalate, and thermosetting resins such as phenol resin, epoxy resin, silicone resin, and unsaturated polyester.

The housing 104 is an exterior member that covers the needle assembly 20, the moving member 103, the biasing member 105, the detector 106, and the sensor 300 which is to be described later. As shown in FIGS. 16 to 19, the housing 104 of the present embodiment includes a cylindrical member 71 that covers the periphery of the needle assembly 20, the moving member 103, the biasing member 105, the detector 106, and the sensor 300 to be described later in the radial direction D in a state where the puncture needle 1 is at the standby position (see FIG. 16), and a base plate 72 that covers an end surface of the cylindrical member 71 in the insertion direction A1.

The surface of the base plate 72 on the insertion direction A1 side is formed of a contact surface 72a that is brought into contact with the living body surface BS when the puncture needle 1 and the sensor 300 are inserted into the living body. A through hole 74 penetrating in the longitudinal direction A is formed in the base plate 72. When the puncture needle 1 at the standby position (see FIG. 16) moves to the insertion position (see FIG. 18), the puncture needle 1 protrudes from the contact surface 72a in the insertion direction A1 through the through hole 74. The contact surface 72a includes a sticking portion for being indwelled on the living body surface BS.

In addition, the housing 104 of the present embodiment has a configuration in which the cylindrical member 71 and the base plate 72 are detachable, but is not limited to this configuration. Both the cylindrical member 71 and the base plate 72 may be integrally formed. However, by making both detachable, the size of the portion indwelled on the living body surface BS can be easily reduced, and the burden on the subject can be reduced.

Examples of the material of the housing 104 include a resin material. Examples of the resin material include thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluororesin, polycarbonate, polyamide, acetal resin, acrylic resin, and polyethylene terephthalate, and thermosetting resins such as phenol resin, epoxy resin, silicone resin, and unsaturated polyester.

The biasing member 105 of the present embodiment is elastically deformable in the longitudinal direction A. The biasing member 105 of the present embodiment is a coil spring that elastically deforms in the longitudinal direction A. The coil spring as the biasing member 105 is disposed between the hub 50 of the needle assembly 20 and the base plate 72 of the housing 104. Therefore, the coil spring as the biasing member 105 of the present embodiment is compressed and deformed when the puncture needle 1 moves from the standby position (see FIG. 16) to the insertion position (see FIG. 18). Furthermore, by releasing a restoring force of the coil spring as the biasing member 105 in a state where the puncture needle 1 is at the insertion position (see FIG. 18), the puncture needle 1 can be moved from the insertion position (see FIG. 18) in the removal direction A2.

Therefore, in the puncture tool 100 of the present embodiment, when the puncture needle 1 and the sensor 300 are inserted into the living body, the needle assembly 20 and the moving member 103 are moved in the insertion direction A1 against the restoring force of the coil spring as the biasing member 105. As a result, as shown in FIGS. 17 and 18, the needle assembly 20 and the moving member 103 move in the insertion direction A1, and the puncture needle 1 and the sensor 300 are inserted into the living body. Then, after the puncture needle 1 and the sensor 300 are inserted into the living body, the pressing force in the insertion direction A1 applied to the needle assembly 20 and the moving member 103 is released, so that the needle assembly 20 and the moving member 103 are moved in the removal direction A2 by the restoring force of the coil spring as the biasing member 105. As a result, the puncture needle 1 can be removed from the living body in a state where the sensor 300 remains in the living body. In the present embodiment, due to the restoring force of the coil spring as the biasing member 105, the puncture needle 1 returns from the insertion position (see FIG. 18) to the position accommodated in the housing 104 (for example, the same standby position as in FIG. 16) (see FIG. 19).

The detector 106 is operatively connected with the sensor 300. Specifically, the detector 106 is coupled to the sensor 300 via a contact portion 90 including, for example, a conductive plate, an electric signal line, and the like. The contact portion 90 connects the detector 106 and the sensor 300 through the slit 2b of the puncture needle 1. Therefore, the detector 106 can receive detection information of the sensor 300 from the sensor 300 indwelled in the living body. Furthermore, as described above, the detector 106 analyzes the detection signal received from the sensor 300, and transmits the analysis result to an external device such as a display device as necessary. The detector 106 includes a processor, a memory, a battery, and the like. As described above, the detector 106 may be provided not on the base plate 72 but on a side of a separate transmitter that can be combined with the base plate 72. In this case, instead of the detector 106, only the contact portion to the transmitter is previously placed on the base plate 72 by the puncture tool 100.

As shown in FIGS. 16 to 19, the detector 106 of the present embodiment moves in the insertion direction A1 together with the puncture needle 1 and the sensor 300 when the puncture needle 1 and the sensor 300 are inserted into the living body. More specifically, the detector 106 of the present embodiment is retained by the hub 50 with the puncture needle 1 being at the standby position (see FIG. 16). When the puncture needle 1 moves from the standby position (see FIG. 16) to the insertion position (see FIG. 18), the detector 106 moves in the insertion direction A1 together with the needle assembly 20. When the puncture needle 1 reaches the insertion position (see FIG. 18), the detector 106 is engaged with the base plate 72 of the housing 104, and the state of being retained by the needle assembly 20 is released. Any means such as adhesion and mechanical engagement can be adopted as the engagement means between the detector 106 and the base plate 72. As a result, the detector 106 is retained on the base plate 72. Therefore, when the puncture needle 1 is removed from the living body, that is, when the puncture needle 1 returns from the insertion position to the standby position, although the needle assembly 20 moves in the removal direction A2, the detector 106 does not move in the removal direction A2 and remains on the base plate 72 of the housing 104.

The sensor 300 of the present embodiment is a wire-shaped member having a small diameter accommodated in the puncture needle 1. As the sensor 300, a member that detects an electrical signal corresponding to the amount or concentration of the substance to be measured can be used. The sensor 300 extends in the puncture needle 1 in the longitudinal direction A of the puncture needle 1.

The sensor 300 may be, for example, a wire electrode having a circular cross-sectional shape. The wire electrode is accommodated in the puncture needle 1. The outer diameter of the wire electrode may be, for example, 0.02 mm to 0.2 mm. For example, two wire electrodes of a working electrode and a reference electrode may be accommodated in the puncture needle 1. The working electrode may be configured based on a core material having a conductive surface, and may be configured to include a sensing unit configured to detect a substance to be measured on an outer wall of the core material, and a protective portion in which the outer wall of the core material is coated with an insulating material. The sensing unit can detect a change in electrical characteristic with respect to the substance to be measured. The sensing unit is formed on the surface of the core material by using a thin film forming means such as dipping, electrolytic polymerization, or sputtering. A reagent that specifically reacts with the substance to be measured is applied to the surface of the working electrode. When the substance to be measured is glucose, a reagent containing glucose oxidase or a phenylboronic acid compound is used. The reference electrode is used as a reference electrode for the working electrode described above. A reference electrode or a counter electrode may be wound around the working electrode in a coil shape to form one wire electrode. In addition, the puncture needle 1 itself may be used as the reference electrode or the counter electrode. Information on the substance to be measured detected by the sensing unit of the working electrode is transmitted to the detector 106.

The puncture needle and the needle assembly according to the present disclosure are not limited to the specific configurations shown in the above-described embodiments, and various modifications, changes, and combinations are possible without departing from the scope of the claims.

Aspects of the puncture needle and the needle assembly according to the present disclosure are as follows.

Aspect 1. A puncture needle comprising:

a puncture portion having a blade surface at a tip end surface and a slit extending to the tip end surface; and a retained portion connected to a base end of the puncture portion and configured to be retained by a hub, the retained portion including:

a tubular portion having a substantially constant outer diameter larger than a maximum outer diameter of the puncture portion, and a tapered portion located between the puncture portion and the tubular portion, an outer diameter of the tapered portion gradually decreasing from a tubular-portion side to a puncture-portion side, wherein in a lateral view with the slit facing upward, lower contour lines of the puncture portion, the tubular portion, and the tapered portion are collinear.

Aspect 2. The puncture needle according to Aspect 1, wherein the slit extends from the tip end surface of the puncture portion to the tapered portion of the retained portion.

Aspect 3. The puncture needle according to Aspect 2, wherein the slit terminates at the tapered portion.

Aspect 4. The puncture needle according to Aspect 2 or 3, wherein in the tapered portion, a width of the slit gradually decreases to a side of a base end.

Aspect 5. The puncture needle according to any one of Aspects 1 to 4, wherein an outer diameter of the puncture portion is substantially constant on a side of the base end relative to the tip end surface.

Aspect 6. A needle assembly comprising:

the puncture needle according to any one of Aspects 1 to 5; and a hub for retaining the retained portion of the puncture needle.

The present disclosure relates to a puncture needle and a needle assembly.

REFERENCE CHARACTER LIST

1 Puncture needle
2 Puncture portion
2a Blade surface
2b Slit
3 Retained portion
4 Needle tip
11 Tubular portion
12 Tapered portion
13a, 13b Side wall portion
13c Bottom portion
20 Needle assembly
50 Hub
50a Accommodation space
51 Surrounding wall portion
51a1 Opening
52 Wall end surface
55 Main body portion
56 Locking claw portion
57 Outer flange portion
58 Extending portion
59 Engaging protrusion portion
59a Inclined surface
61 Engaging portion
62 Engaging recess portion
71 Cylindrical member
72 Base plate
72a Contact surface
74 Through hole
90 Contact portion
100 Puncture tool
103 Moving member
104 Housing
105 Biasing member
106 Electronic device
200 Adhesive member
300 Sensor
A Longitudinal direction of puncture needle
A1 Insertion direction
A2 Removal direction
B Circumferential direction of puncture needle
C Width direction of puncture needle
D Radial direction of puncture needle
H1 Distance between contour lines of puncture portion in lateral view with slit of puncture portion facing upward
H2 Distance between contour lines of tubular portions in lateral view with slit of puncture portion facing upward
H3 Distance between contour lines of puncture portion in top view
H4 Distance between contour lines of tubular portions in top view M Common center straight line
R Smallest diameter of hub opening
T1 Outer diameter of puncture portion
T2 Outer diameter of tubular portion
T3 Outer diameter of tapered portion
W Width of slit
BS Living body surface
CL1, CL4, CL7, CL10 Contour line of puncture portion
CL2, CL5, CL8, CL11 Contour line of tubular portion
CL3, CL6, CL9, CL12 Contour line of tapered portion
$\theta 1$ Inclination angle of upper contour line of tapered portion with respect to longitudinal direction in lateral view
$\theta 2$ Inclination angle of contour lines on both sides in width direction of tapered portion with respect to longitudinal direction in top view

The invention claimed is:

1. A needle assembly comprising:
a hub; and
a puncture needle comprising:
a puncture portion comprising:
a distal part comprising a blade surface, and
a proximal part having a substantially constant outer diameter; and
a retained portion connected to the proximal part of the puncture portion and retained by the hub; wherein:
the retained portion comprises:
a tubular portion having a substantially constant outer diameter larger than a maximum outer diameter of the proximal part of the puncture portion, and
a tapered portion located between the proximal part of the puncture portion and the tubular portion, an outer diameter of the tapered portion gradually decreasing from a tubular-portion side to a puncture-portion side;
the puncture portion includes a slit that extends from the distal part of the puncture portion to the hub; and
in a lateral view with the slit facing upward, lower contour lines of the puncture portion, the tubular portion, and the tapered portion are collinear.

2. The needle assembly according to claim 1, wherein the slit terminates at the tapered portion.

3. The needle assembly according to claim 1, wherein, in the tapered portion, a width of the slit gradually decreases to a proximal-end side.

4. The needle assembly according to claim 1, wherein:
a length of the proximal part of the puncture portion having the substantially constant outer diameter is greater than a length of the distal part of the puncture portion.

5. The needle assembly according to claim 1, wherein:
a length of the proximal part of the puncture portion having the substantially constant outer diameter is greater than a length of the tapered portion.

* * * * *